(12) United States Patent
Bremel et al.

(10) Patent No.: US 6,548,740 B1
(45) Date of Patent: *Apr. 15, 2003

(54) METHODS FOR CREATING TRANSGENIC ANIMALS

(75) Inventors: Robert D. Bremel, Waunakee, WI (US); Anthony W.S. Chan, Madison, WI (US); Jane C. Burns, La Jolla, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,264

(22) Filed: Feb. 11, 2000

Related U.S. Application Data

(63) Continuation of application No. 08/821,984, filed on Mar. 20, 1997, now Pat. No. 6,080,912.

(51) Int. Cl.$^7$ .......................... C12N 15/00; C12N 5/00; C12N 5/02; C12N 15/63; A01K 67/027
(52) U.S. Cl. ........................... 800/23; 800/21; 800/25; 800/15; 435/325; 435/455; 435/456
(58) Field of Search .......................... 800/15, 25, 23, 800/21; 435/325, 455, 456

(56) References Cited

U.S. PATENT DOCUMENTS

| | | | |
|---|---|---|---|
| 5,175,384 A | 12/1992 | Krimpenfort et al. | |
| 5,512,421 A | 4/1996 | Burns et al. | |
| 5,523,222 A | 6/1996 | Page et al. | |
| 6,080,912 A | * 6/2000 | Bremel et al. | 800/23 |
| 6,140,552 A | * 10/2000 | Deboer et al. | 800/15 |

FOREIGN PATENT DOCUMENTS

| | | |
|---|---|---|
| WO | 90/08832 | 8/1990 |
| WO | 94/29440 | 12/1994 |

OTHER PUBLICATIONS

RE Haskell et al., Molecular Rep. and Dev., "Efficient Production of Transgenic Cattle by Retroviral Infection of Early Embryos," (1995) 40:386–390.*

JM Coffin et al., Retroviruses, "Integration," (Cold Spring Harbor Lab. Press, Plainview, NY), 1997, Chap. 5, pp. 161–167.*

Adams et al, "Transduction of primary human hepatocytes with amphotropic and xenotropic retroviral vectors," *Proc. Natl. Acad. Sci. USA* 89:8981–8985 (1992).

Bavister and Yanagimachi, "The Effects of Sperm Extracts and Energy Sources on the Motility and Acrosome Reaction of Hamster Spermatozoa in vitro," *Bio. Reprod.* 16:228–237 (1977).

Bavister et al., "Development of Preimplantation Embryos of the ?Golden Hamster in a Defined Culture Medium," *Biol. Reprod.* 28:235–247 (1983).

Brun et al., "The Relationship of Piry Virus to Other Vesiculoviruses: A Re–Evaluation Based on the Glycoprotein Gene Sequence," *Intervirol.* 38:274–282 (1995).

Burns et al., "Vesicular stomatitis virus G glycoprotein pseudotyped retroviral vectors: Concentration to very high titer and efficient gene transfer into mammalian and non–mammalian cells," *Proc. Natl. Acad. Sci. USA* 90:8033–8037 (1993).

Cheng, Doctoral Dissertation, Cambridge Univeristy, Cambridge, United Kingdom (1995) Reference Unavailable.

Coffin, "Molecular Mechanisms of Nucleic Acid Integration," *J. Med. Virol.* 31:43–49 (1990).

Funahashi et al., "In Vitro Development of In Vitro–Matured Porcine Oocytes Following Chemical Activation or In Vitro Fertilization," *Biol. Reprod.* 50:1072–1077 (1994).

Funahashi et al., "Different hormonal requirements of pig oocyte–cumulus complexes during maturation in vitro," *J. Reprod. Fert.* 101:159–165 (1994)

Goff et al., "Isolation and Properties of Moloney Murine Leukemia Virus Mutants: Use of a Rapid Assay for Release of Virion Reverse Transcriptase," *J. Virol.* 38:239–238 (1981).

Graham and Van der Eb, "A New Technique for the Assay of Infectivity of Human Adenovirus 5 DNA," *Virol.* 52:456–467 (1973).

Hajihosseini et al., "Evidence that retroviruses integrate into post–replication host DNA," *EMBO J.* 12:4969–4974 (1993).

Haskell and Bowen, "Efficient Production of Transgenic Cattle by Retroviral Infection of Early Embryos," *Mol. Reprod. Dev.* 40:386–390 (1995).

Hogan et al., Manipulating the Mouse Embryo: A laboratory Manual, 2nd Ed., Cold Spring Harbor Laboratory Press, Cold Spring Harbor, NY, pp. 130–133, 251–252 (1994).

Jaenisch, "Germ line integration and Mendelian transmission of the exogenous Moloney leukemia virus," *Proc. Natl. Acad. Sci. USA* 73:1260–1264 (1976).

Jaenisch et al., "Chromosomal Position and Activation of Retroviral Genomes Inserted into the Germ Line of Mice," *Cell* 24:519–529 (1981).

Jahner et al., "De novo methylation and expression of retroviral genomes during mouse embryogenesis," *Nature* 298:623–628 (1982).

(List continued on next page.)

*Primary Examiner*—Scott D. Priebe
*Assistant Examiner*—Peter Paras, Jr.
(74) *Attorney, Agent, or Firm*—Quarles & Brady LLP

(57) ABSTRACT

The present invention provides improved methods and compositions for the generation of transgenic non-human animals. The present invention permits the introduction of exogenous nucleic acid sequences into the genome of unfertilized eggs (e.g., pre-maturation oocytes and pre-fertilization oocytes) by microinjection of infectious retrovirus into the perivitelline space of the egg. The methods of the present invention provide an increased efficiency of production of transgenic animals with a reduced rate of generating animals which are mosaic for the presence of the transgene.

11 Claims, 3 Drawing Sheets

OTHER PUBLICATIONS

Jahner et al., "Insertion of the bacterial gpt gene into the germ line of mice by retroviral infection," *Proc. Natl. Acad. Sci. USA* 82:6927–6931 (1985).

Keskintepe et al., "In vitro development of morulae from immature caprine oocytes," *Zygotes* 2:97–102 (1994).

Kim et al., "Gene Transfer in Bovine Blastocysts Using Replication–Defective Retroviral Vectors Packaged with Gibbon Ape Leukemia Virus Envelopes," *Mol. Reprod. Develop.* 35:105–113 (1993).

Kulkosky and Skalka, "Molecular Mechanism of Retroviral DNA Integration," *Pharmac. Ther.* 61:185–203 (1994).

Leibfried and Bavister, "Effects of epinephrine and hypotaurine on in vitro fertilization in the golden hamster," *J. Reprod. Fert.* 66:87–93 (1982).

Markowitz et al, "A Safe Packaging Line for Gene Transfer: Separating Viral Genes on Two Different Plasmids," *J. Virol.* 62::1120–1124 (1988).

Masters et al., "Structure and Expression of the glycoprotein Gene of Chandipura Virus," *Virol.* 171:285–290 (1989).

Mastromarino et al, "Characterization of Membrane Components of the Erythrocyte Involved in Vesicular Stomatitis Virus Attachment and Fusion at Acidic pH," *J. Gen. Virol.* 68:2359–2369 (1987).

Mebatsion et al., "Mokola Virus Glycoprotein and Chimeric Proteins Can Replace Rabies Virus Glycoprotein in the Rescue of Infectious Defective Rabies Virus Particles," *J. Virol.* 69:1444–1451 (1995).

Miller and Baltimore, "Redesign of Retrovirus Packaging Cell Lines to Avoid Recombination Leading to Helper Virus Production," *Mol. Cell. Biol.* 6:2895–2902 (1986).

Miller and Rosman, "Improved Retroviral Vectors for Gene Transfer and Expression," *BioTechniques* 7:980–990 (1989).

Miller et al., "Gene Transfer by Retrovirus Vectors Occurs Only in Cells that Are Actively Replicating at the Time of Infection," *Mol. Cell. Biol.* 10:4239–4242 (1990).

Miller, "Human gene therapy comes of age," *Nature* 357:455–560 (1992).

Naldini et al., "In Vivo Gene Delivery and Stable Transduction of Nondividing Cells by a Lentiviral Vector," *Science* 272:263–267 (1996).

Parrish et al., "Effect of Heparin and Chondroitin Sulfate on the Acrosome Reaction and Fertility of Bovine Sperm In Vitro," *Theriogenology* 24:537–549 (1985).

Pyrciak et al., "Retroviral integration into minichromosomes in vitro," *Embro J.* 11:291–303 (1992).

Quade, "Transformation of Mammalian Cells by Avian Myelocytomatosis Virus and Avian Erythrobiastosis Virus," *Virol.* 98:461–465 (1979).

Roe et al., "Integration of murine leukemia virus DNA depends on mitosis," *EMBO J.* 12:2099–2108 (1993).

Rosekrans and First, "Effect of Free Amino Aids and Vitamins on Cleavage and Developmental Rate of Bovine Zygotes in Vitro," *J. Ani. Sci.* 72:434–437 (1994).

Shuman, "Production of transgenic birds," *Eperientia* 47:897–905 (1991).

Simonsen et al., "Isolation and expression of an altered mouse dihydrofolate reductase cDNA," *Proc. Natl. Acad. Sci. USA* 80:2495–2499 (1983).

Stewart et al., "Expression of retroviral vectors in transgenic mice obtained by embryo infection," *EMBO J.* 6:383–388 (1987).

Stuhlmann et al., "Introduction of a selectable gene into different animal tissue by a retrovirus recombinant vector," *Proc. Natl. Acad. Sci. USA* 81:7151–7155 (1984).

Van der Putten et al, "Efficient insertion of genes into the mouse germ line via retroviral vectors," *Proc. Natl. Acad. Sci. USA* 82:6148–6152 (1985).

Wall et al., "Making Transgenic Livestock: Genetic Engineering on a Large Scale," *J. Cell Biochem.* 49:113–120 (1992).

Xu et al., "Factors Affecting Long–Term Stability of Moloney Murine Leukemia Virus–Based Vectors," *Virol.* 171:331–341 (1989).

Yee et al., "Generation of Hihg–Titer Pseudotyped Retroviral Vector with Very Broad Host Range," *Meth. Cell Biol.* 43:99–112 (1994).

\* cited by examiner

```
                              SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 1:

GCATTGCATC AGCCATGATG                                                   20

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 2:
```

```
GATGGATTGC ACGCAGGTTC                                                    20

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO: 3:

GGCTATCGCT GGATGTGTCT                                                    20

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO: 4:

ACTGAACAAA TGGCACTAGT                                                    20

(2) INFORMATION FOR SEQ ID NO: 5:

(i) SEQUENCE CHARACTERISTICS:
        (A) LENGTH: 1590 base pairs
        (B) TYPE: nucleic acid
        (C) STRANDEDNESS: double
        (D) TOPOLOGY: linear (ii) MOLECULE TYPE: other nucleic acid
         (A) DESCRIPTION: /desc = "DNA"

(ix) FEATURE:
         (A) NAME/KEY: CDS
         (B) LOCATION: 1..1587

(xi) SEQUENCE DESCRIPTION: SEQ ID NO: 5:

ATG GAT CTC TTT CCC ATT TTG GTC GTG GTG CTC ATG ACA GAT ACT GTC         48
Met Asp Leu Phe Pro Ile Leu Val Val Val Leu Met Thr Asp Thr Val
 1               5                  10                  15

TTA GGG AAG TTT CAA ATT GTC TTC CCG GAT CAG AAT GAA CTG GAG TGG         96
Leu Gly Lys Phe Gln Ile Val Phe Pro Asp Gln Asn Glu Leu Glu Trp
             20                  25                  30

AGA CCA GTT GTG GGT GAC TCT CGG CAT TGC CCA CAG TCA TCA GAA ATG        144
Arg Pro Val Val Gly Asp Ser Arg His Cys Pro Gln Ser Ser Glu Met
         35                  40                  45

CAA TTC GAT GGA AGC AGA TCC CAG ACC ATA CTG ACT GGG AAA GCT CCC        192
Gln Phe Asp Gly Ser Arg Ser Gln Thr Ile Leu Thr Gly Lys Ala Pro
     50                  55                  60

GTG GGG ATC ACG CCC TCT AAA TCA GAT GGA TTT ATC TGC CAT GCC GCA        240
Val Gly Ile Thr Pro Ser Lys Ser Asp Gly Phe Ile Cys His Ala Ala
 65                  70                  75                  80

AAA TGG GTG ACA ACA TGT GAT TTC AGG TGG TAT GGG CCG AAA TAC ATC        288
Lys Trp Val Thr Thr Cys Asp Phe Arg Trp Tyr Gly Pro Lys Tyr Ile
                 85                  90                  95

ACT CAT TCA ATA CAT CAT CTG AGA CCG ACA ACA TCA GAC TGT GAG ACA        336
Thr His Ser Ile His His Leu Arg Pro Thr Thr Ser Asp Cys Glu Thr
            100                 105                 110
```

```
GCT CTC CAA AGG TAT AAA GAT GGG AGC TTA ATC AAT CTT GGA TTC CCC      384
Ala Leu Gln Arg Tyr Lys Asp Gly Ser Leu Ile Asn Leu Gly Phe Pro
        115                 120                 125

CCA GAA TCC TGC GGT TAT GCA ACA GTC ACA GAT TCT GAG GCA ATG TTG      432
Pro Glu Ser Cys Gly Tyr Ala Thr Val Thr Asp Ser Glu Ala Met Leu
    130                 135                 140

GTC CAA GTG ACT CCC CAC CAC GTT GGG GTG GAT GAT TAT AGA GGT CAC      480
Val Gln Val Thr Pro His His Val Gly Val Asp Asp Tyr Arg Gly His
145                 150                 155                 160

TGG ATC GAC CCA CTA TTT CCA GGA GGA GAA TGC TCC ACC AAT TTT TGT      528
Trp Ile Asp Pro Leu Phe Pro Gly Gly Glu Cys Ser Thr Asn Phe Cys
                165                 170                 175

GAT ACA GTC CAC AAT TCA TCG GTG TGG ATC CCC AAG AGT CAA AAG ACT      576
Asp Thr Val His Asn Ser Ser Val Trp Ile Pro Lys Ser Gln Lys Thr
            180                 185                 190

GAC ATC TGT GCC CAG TCT TTC AAA AAT ATC AAG ATG ACC GCA TCT TAC      624
Asp Ile Cys Ala Gln Ser Phe Lys Asn Ile Lys Met Thr Ala Ser Tyr
        195                 200                 205

CCC TCA GAA GGA GCA TTG GTG AGT GAC AGA TTT GCC TTC CAC AGT GCA      672
Pro Ser Glu Gly Ala Leu Val Ser Asp Arg Phe Ala Phe His Ser Ala
    210                 215                 220

TAT CAT CCA AAT ATG CCG GGG TCA ACT GTT TGC ATA ATG GAC TTT TGC      720
Tyr His Pro Asn Met Pro Gly Ser Thr Val Cys Ile Met Asp Phe Cys
225                 230                 235                 240

GAA CAA AAG GGG TTG AGA TTC ACA AAT GGA GAG TGG ATG GGT CTC AAT      768
Glu Gln Lys Gly Leu Arg Phe Thr Asn Gly Glu Trp Met Gly Leu Asn
                245                 250                 255

GTG GAG CAA TCC ATC CGA GAG AAG AAG ATA AGT GCC ATC TTC CCA AAT      816
Val Glu Gln Ser Ile Arg Glu Lys Lys Ile Ser Ala Ile Phe Pro Asn
            260                 265                 270

TGT GTT GCA GGG ACT GAA ATC CGA GCC ACA CTA GAA TCA GAA GGG GCA      864
Cys Val Ala Gly Thr Glu Ile Arg Ala Thr Leu Glu Ser Glu Gly Ala
        275                 280                 285

AGA ACT TTG ACG TGG GAG ACT CAA AGA ATG CTA GAT TAC TCT TTG TGT      912
Arg Thr Leu Thr Trp Glu Thr Gln Arg Met Leu Asp Tyr Ser Leu Cys
    290                 295                 300

CAG AAC ACC TGG GAC AAA GTT TCC AGG AAA GAA CCT CTC AGT CCG CTT      960
Gln Asn Thr Trp Asp Lys Val Ser Arg Lys Glu Pro Leu Ser Pro Leu
305                 310                 315                 320

GAC TTG AGC TAT CTG TCA CCA AGG GCT CCA GGG AAA GGC ATG GCC TAT     1008
Asp Leu Ser Tyr Leu Ser Pro Arg Ala Pro Gly Lys Gly Met Ala Tyr
                325                 330                 335

ACC GTC ATA AAC GGA ACC CTG CAT TCG GCT CAT GCT AAA TAC ATT AGA     1056
Thr Val Ile Asn Gly Thr Leu His Ser Ala His Ala Lys Tyr Ile Arg
            340                 345                 350

ACC TGG ATT GAT TAT GGA GAA ATG AAG GAA ATT AAA GGT GGA CGT GGA     1104
Thr Trp Ile Asp Tyr Gly Glu Met Lys Glu Ile Lys Gly Gly Arg Gly
        355                 360                 365

GAA TAT TCC AAG GCT CCT GAG CTC CTC TGG TCC CAG TGG TTC GAT TTT     1152
Glu Tyr Ser Lys Ala Pro Glu Leu Leu Trp Ser Gln Trp Phe Asp Phe
    370                 375                 380

GGA CCG TTC AAA ATT GGA CCG AAT GGA CTC CTG CAC ACA GGG AAA ACC     1200
Gly Pro Phe Lys Ile Gly Pro Asn Gly Leu Leu His Thr Gly Lys Thr
385                 390                 395                 400

TTT AAA TTC CCT CTT TAT TTG ATC GGA GCA GGC ATA ATT GAC GAA GAT     1248
Phe Lys Phe Pro Leu Tyr Leu Ile Gly Ala Gly Ile Ile Asp Glu Asp
                405                 410                 415

CTG CAT GAA CTA GAT GAG GCT GCT CCC ATT GAT CAC CCA CAA ATG CCT     1296
Leu His Glu Leu Asp Glu Ala Ala Pro Ile Asp His Pro Gln Met Pro
```

```
                     420                425                430
GAC GCG AAA AGC GTT CTT CCA GAA GAT GAA GAG ATA TTC TTC GGA GAC        1344
Asp Ala Lys Ser Val Leu Pro Glu Asp Glu Glu Ile Phe Phe Gly Asp
        435                 440                 445

ACA GGT GTA TCC AAA AAC CCT ATC GAG TTG ATT CAA GGA TGG TTC TCA        1392
Thr Gly Val Ser Lys Asn Pro Ile Glu Leu Ile Gln Gly Trp Phe Ser
    450                 455                 460

AAT TGG AGA GAG AGT GTA ATG GCA ATA GTC GGA ATT GTT CTA CTC ATC        1440
Asn Trp Arg Glu Ser Val Met Ala Ile Val Gly Ile Val Leu Leu Ile
465                 470                 475                 480

GTT GTG ACA TTT CTG GCG ATC AAG ACG GTC CGG GTG CTT AAT TGT CTC        1488
Val Val Thr Phe Leu Ala Ile Lys Thr Val Arg Val Leu Asn Cys Leu
                485                 490                 495

TGG AGA CCC AGA AAG AAA AGA ATC GTC AGA CAA GAA GTA GAT GTT GAA        1536
Trp Arg Pro Arg Lys Lys Arg Ile Val Arg Gln Glu Val Asp Val Glu
            500                 505                 510

TCC CGA CTA AAC CAT TTT GAG ATG AGA GGC TTT CCT GAA TAT GTT AAG        1584
Ser Arg Leu Asn His Phe Glu Met Arg Gly Phe Pro Glu Tyr Val Lys
        515                 520                 525

AGA TAA                                                                1590
Arg
```

(2) INFORMATION FOR SEQ ID NO: 6:

(i) SEQUENCE CHARACTERISTICS:
        (A) LENGTH: 529 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Asp Leu Phe Pro Ile Leu Val Val Leu Met Thr Asp Thr Val
 1               5                  10                  15

Leu Gly Lys Phe Gln Ile Val Phe Pro Asp Gln Asn Glu Leu Glu Trp
                 20                  25                  30

Arg Pro Val Val Gly Asp Ser Arg His Cys Pro Gln Ser Ser Glu Met
             35                  40                  45

Gln Phe Asp Gly Ser Arg Ser Gln Thr Ile Leu Thr Gly Lys Ala Pro
         50                  55                  60

Val Gly Ile Thr Pro Ser Lys Ser Asp Gly Phe Ile Cys His Ala Ala
 65                  70                  75                  80

Lys Trp Val Thr Thr Cys Asp Phe Arg Trp Tyr Gly Pro Lys Tyr Ile
                 85                  90                  95

Thr His Ser Ile His His Leu Arg Pro Thr Thr Ser Asp Cys Glu Thr
             100                 105                 110

Ala Leu Gln Arg Tyr Lys Asp Gly Ser Leu Ile Asn Leu Gly Phe Pro
         115                 120                 125

Pro Glu Ser Cys Gly Tyr Ala Thr Val Thr Asp Ser Glu Ala Met Leu
     130                 135                 140

Val Gln Val Thr Pro His Val Gly Val Asp Asp Tyr Arg Gly His
145                 150                 155                 160

Trp Ile Asp Pro Leu Phe Pro Gly Gly Glu Cys Ser Thr Asn Phe Cys
                 165                 170                 175

Asp Thr Val His Asn Ser Ser Val Trp Ile Pro Lys Ser Gln Lys Thr
             180                 185                 190

Asp Ile Cys Ala Gln Ser Phe Lys Asn Ile Lys Met Thr Ala Ser Tyr
         195                 200                 205
```

```
Pro Ser Glu Gly Ala Leu Val Ser Asp Arg Phe Ala Phe His Ser Ala
    210                 215                 220

Tyr His Pro Asn Met Pro Gly Ser Thr Val Cys Ile Met Asp Phe Cys
225                 230                 235                 240

Glu Gln Lys Gly Leu Arg Phe Thr Asn Gly Glu Trp Met Gly Leu Asn
                245                 250                 255

Val Glu Gln Ser Ile Arg Glu Lys Lys Ile Ser Ala Ile Phe Pro Asn
                260                 265                 270

Cys Val Ala Gly Thr Glu Ile Arg Ala Thr Leu Glu Ser Glu Gly Ala
            275                 280                 285

Arg Thr Leu Thr Trp Glu Thr Gln Arg Met Leu Asp Tyr Ser Leu Cys
290                 295                 300

Gln Asn Thr Trp Asp Lys Val Ser Arg Lys Glu Pro Leu Ser Pro Leu
305                 310                 315                 320

Asp Leu Ser Tyr Leu Ser Pro Arg Ala Pro Gly Lys Gly Met Ala Tyr
                325                 330                 335

Thr Val Ile Asn Gly Thr Leu His Ser Ala His Ala Lys Tyr Ile Arg
                340                 345                 350

Thr Trp Ile Asp Tyr Gly Glu Met Lys Glu Ile Lys Gly Gly Arg Gly
            355                 360                 365

Glu Tyr Ser Lys Ala Pro Glu Leu Leu Trp Ser Gln Trp Phe Asp Phe
370                 375                 380

Gly Pro Phe Lys Ile Gly Pro Asn Gly Leu Leu His Thr Gly Lys Thr
385                 390                 395                 400

Phe Lys Phe Pro Leu Tyr Leu Ile Gly Ala Gly Ile Ile Asp Glu Asp
                405                 410                 415

Leu His Glu Leu Asp Glu Ala Ala Pro Ile Asp His Pro Gln Met Pro
                420                 425                 430

Asp Ala Lys Ser Val Leu Pro Glu Asp Glu Ile Phe Phe Gly Asp
            435                 440                 445

Thr Gly Val Ser Lys Asn Pro Ile Glu Leu Ile Gln Gly Trp Phe Ser
    450                 455                 460

Asn Trp Arg Glu Ser Val Met Ala Ile Val Gly Ile Val Leu Leu Ile
465                 470                 475                 480

Val Val Thr Phe Leu Ala Ile Lys Thr Val Arg Val Leu Asn Cys Leu
                485                 490                 495

Trp Arg Pro Arg Lys Lys Arg Ile Val Arg Gln Glu Val Asp Val Glu
            500                 505                 510

Ser Arg Leu Asn His Phe Glu Met Arg Gly Phe Pro Glu Tyr Val Lys
            515                 520                 525

Arg (2) INFORMATION FOR SEQ ID NO: 7:

(i) SEQUENCE CHARACTERISTICS:
        (A) LENGTH: 1590 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 1..1587
```

(xi) SEQUENCE DESCRIPTION: SEQ ID NO: 7:

```
ATG GAT CTC TTT CCC ATT TTG GTC GTG GTG CTC ATG ACA GAT ACT GTC      48
Met Asp Leu Phe Pro Ile Leu Val Val Val Leu Met Thr Asp Thr Val
 1               5                  10                  15

TTA GGG AAG TTT CAA ATT GTC TTC CCG GAT CAG AAT GAA CTG GAG TGG      96
Leu Gly Lys Phe Gln Ile Val Phe Pro Asp Gln Asn Glu Leu Glu Trp
             20                  25                  30

AGA CCA GTT GTG GGT GAC TCT CGG CAT TGC CCA CAG TCA TCA GAA ATG     144
Arg Pro Val Val Gly Asp Ser Arg His Cys Pro Gln Ser Ser Glu Met
         35                  40                  45

CAA TTC GAT GGA AGC AGA TCC CAG ACC ATA CTG ACT GGG AAA GCT CCC     192
Gln Phe Asp Gly Ser Arg Ser Gln Thr Ile Leu Thr Gly Lys Ala Pro
     50                  55                  60

GTG GGG ATC ACG CCC TCT AAA TCA GAT GGA TTT ATC TGC CAT GCC GCA     240
Val Gly Ile Thr Pro Ser Lys Ser Asp Gly Phe Ile Cys His Ala Ala
 65                  70                  75                  80

AAA TGG GTG ACA ACA TGT GAT TTC AGG TGG TAT GGG CCG AAA TAC ATC     288
Lys Trp Val Thr Thr Cys Asp Phe Arg Trp Tyr Gly Pro Lys Tyr Ile
                 85                  90                  95

ACT CAT TCA ATA CAT CAT CTG AGA CCG ACA ACA TCA GAC TGT GAG ACA     336
Thr His Ser Ile His His Leu Arg Pro Thr Thr Ser Asp Cys Glu Thr
            100                 105                 110

GCT CTC CAA AGG TAT AAA GAT GGG AGC TTA ATC AAT CTT GGA TTC CCC     384
Ala Leu Gln Arg Tyr Lys Asp Gly Ser Leu Ile Asn Leu Gly Phe Pro
        115                 120                 125

CCA GAA TCC TGC GGT TAT GCA ACA GTC ACA GAT TCT GAG GCA ATG TTG     432
Pro Glu Ser Cys Gly Tyr Ala Thr Val Thr Asp Ser Glu Ala Met Leu
    130                 135                 140

GTC CAA GTG ACT CCC CAC CAC GTT GGG GTG GAT GAT TAT AGA GGT CAC     480
Val Gln Val Thr Pro His His Val Gly Val Asp Asp Tyr Arg Gly His
145                 150                 155                 160

TGG ATC GAC CCA CTA TTT CCA GGA GGA GAA TGC TCC ACC AAT TTT TGT     528
Trp Ile Asp Pro Leu Phe Pro Gly Gly Glu Cys Ser Thr Asn Phe Cys
                165                 170                 175

GAT ACA GTC CAC AAT TCA TCG GTG TGG ATC CCC AAG AGT CAA AAG ACT     576
Asp Thr Val His Asn Ser Ser Val Trp Ile Pro Lys Ser Gln Lys Thr
            180                 185                 190

GAC ATC TGT GCC CAG TCT TTC AAA AAT ATC AAG ATG ACC GCA TCT TAC     624
Asp Ile Cys Ala Gln Ser Phe Lys Asn Ile Lys Met Thr Ala Ser Tyr
        195                 200                 205

CCC TCA GAA GGA GCA TTG GTG AGT GAC AGA TTT GCC TTC CAC AGT GCA     672
Pro Ser Glu Gly Ala Leu Val Ser Asp Arg Phe Ala Phe His Ser Ala
    210                 215                 220

TAT CAT CCA AAT ATG CCG GGG TCA ACT GTT TGC ATA ATG GAC TTT TGC     720
Tyr His Pro Asn Met Pro Gly Ser Thr Val Cys Ile Met Asp Phe Cys
225                 230                 235                 240

GAA CAA AAG GGG TTG AGA TTC ACA AAT GGA GAG TGG ATG GGT CTC AAT     768
Glu Gln Lys Gly Leu Arg Phe Thr Asn Gly Glu Trp Met Gly Leu Asn
                245                 250                 255

GTG GAG CAA TCC ATC CGA GAG AAG AAG ATA AGT GCC ATC TTC CCA AAT     816
Val Glu Gln Ser Ile Arg Glu Lys Lys Ile Ser Ala Ile Phe Pro Asn
            260                 265                 270

TGT GTT GCA GGG ACT GAA ATC CGA GCC ACA CTA GAA TCA GAA GGG GCA     864
Cys Val Ala Gly Thr Glu Ile Arg Ala Thr Leu Glu Ser Glu Gly Ala
        275                 280                 285

AGA ACT TTG ACG TGG GAG ACT CAA AGA ATG CTA GAT TAC TCT TTG TGT     912
Arg Thr Leu Thr Trp Glu Thr Gln Arg Met Leu Asp Tyr Ser Leu Cys
    290                 295                 300

CAG AAC ACC TGG GAC AAA GTT TCC AGG AAA GAA CCT CTC AGT CCG CTT     960
```

-continued

```
Gln Asn Thr Trp Asp Lys Val Ser Arg Lys Glu Pro Leu Ser Pro Leu
305                 310                 315                 320

GAC TTG AGC TAT CTG TCA CCA AGG GCT CCA GGG AAA GGC ATG GCC TAT    1008
Asp Leu Ser Tyr Leu Ser Pro Arg Ala Pro Gly Lys Gly Met Ala Tyr
                325                 330                 335

ACC GTC ATA AAC GGA ACC CTG CAT TCG GCT CAT GCT AAA TAC ATT AGA    1056
Thr Val Ile Asn Gly Thr Leu His Ser Ala His Ala Lys Tyr Ile Arg
                340                 345                 350

ACC TGG ATT GAT TAT GGA GAA ATG AAG GAA ATT AAA GGT GGA CGT GGA    1104
Thr Trp Ile Asp Tyr Gly Glu Met Lys Glu Ile Lys Gly Gly Arg Gly
            355                 360                 365

GAA TAT TCC AAG GCT CCT GAG CTC CTC TGG TCC CAG TGG TTC GAT TTT    1152
Glu Tyr Ser Lys Ala Pro Glu Leu Leu Trp Ser Gln Trp Phe Asp Phe
        370                 375                 380

GGA CCG TTC AAA ATT GGA CCG AAT GGA CTC CTG CAC ACA GGG AAA ACC    1200
Gly Pro Phe Lys Ile Gly Pro Asn Gly Leu Leu His Thr Gly Lys Thr
385                 390                 395                 400

TTT AAA TTC CCT CTT TAT TTG ATC GGA GCA GGC ATA ATT GAC GAA GAT    1248
Phe Lys Phe Pro Leu Tyr Leu Ile Gly Ala Gly Ile Ile Asp Glu Asp
                405                 410                 415

CTG CAT GAA CTA GAT GAG GCT GCT CCC ATT GAT CAC CCA CAA ATG CCT    1296
Leu His Glu Leu Asp Glu Ala Ala Pro Ile Asp His Pro Gln Met Pro
                420                 425                 430

GAC GCG AAA AGC GTT CTT CCA GAA GAT GAA GAG ATA TTC TTC GGA GAC    1344
Asp Ala Lys Ser Val Leu Pro Glu Asp Glu Glu Ile Phe Phe Gly Asp
            435                 440                 445

ACA GGT GTA TCC AAA AAC CCT ATC GAG TTG ATT CAA GGA TGG TTC TCA    1392
Thr Gly Val Ser Lys Asn Pro Ile Glu Leu Ile Gln Gly Trp Phe Ser
450                 455                 460

AAT TGG AGA GAG AGT GTA ATG GCA ATA GTC GGA ATT GTT CTA CTC ATC    1440
Asn Trp Arg Glu Ser Val Met Ala Ile Val Gly Ile Val Leu Leu Ile
465                 470                 475                 480

GTT GTG ACA TTT CTG GCG ATC AAG ACG TCC CGG GTG CTT AAT TGT CTC    1488
Val Val Thr Phe Leu Ala Ile Lys Thr Val Arg Val Leu Asn Cys Leu
                485                 490                 495

TGG AGA CCC AGA AAG AAA AGA ATC GTC AGA CAA GAA GTA GAT GTT GAA    1536
Trp Arg Pro Arg Lys Lys Arg Ile Val Arg Gln Glu Val Asp Val Glu
                500                 505                 510

TCC CGA CTA AAC CAT TTT GAG ATG AGA GGC TTT CCT GAA TAT GTT AAG    1584
Ser Arg Leu Asn His Phe Glu Met Arg Gly Phe Pro Glu Tyr Val Lys
            515                 520                 525

AGA TAA                                                             1590
Arg
```

(2) INFORMATION FOR SEQ ID NO: 8:

(i) SEQUENCE CHARACTERISTICS:
        (A) LENGTH: 529 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Asp Leu Phe Pro Ile Leu Val Val Leu Met Thr Asp Thr Val
 1               5                  10                  15

Leu Gly Lys Phe Gln Ile Val Phe Pro Asp Gln Asn Glu Leu Glu Trp
                20                  25                  30

Arg Pro Val Val Gly Asp Ser Arg His Cys Pro Gln Ser Ser Glu Met
            35                  40                  45
```

-continued

```
Gln Phe Asp Gly Ser Arg Ser Gln Thr Ile Leu Thr Gly Lys Ala Pro
 50                  55                  60

Val Gly Ile Thr Pro Ser Lys Ser Asp Gly Phe Ile Cys His Ala Ala
 65                  70                  75                  80

Lys Trp Val Thr Thr Cys Asp Phe Arg Trp Tyr Gly Pro Lys Tyr Ile
                 85                  90                  95

Thr His Ser Ile His His Leu Arg Pro Thr Thr Ser Asp Cys Glu Thr
            100                 105                 110

Ala Leu Gln Arg Tyr Lys Asp Gly Ser Leu Ile Asn Leu Gly Phe Pro
        115                 120                 125

Pro Glu Ser Cys Gly Tyr Ala Thr Val Thr Asp Ser Glu Ala Met Leu
    130                 135                 140

Val Gln Val Thr Pro His Val Gly Val Asp Asp Tyr Arg Gly His
145                 150                 155                 160

Trp Ile Asp Pro Leu Phe Pro Gly Gly Glu Cys Ser Thr Asn Phe Cys
                165                 170                 175

Asp Thr Val His Asn Ser Ser Val Trp Ile Pro Lys Ser Gln Lys Thr
            180                 185                 190

Asp Ile Cys Ala Gln Ser Phe Lys Asn Ile Lys Met Thr Ala Ser Tyr
        195                 200                 205

Pro Ser Glu Gly Ala Leu Val Ser Asp Arg Phe Ala Phe His Ser Ala
    210                 215                 220

Tyr His Pro Asn Met Pro Gly Ser Thr Val Cys Ile Met Asp Phe Cys
225                 230                 235                 240

Glu Gln Lys Gly Leu Arg Phe Thr Asn Gly Glu Trp Met Gly Leu Asn
                245                 250                 255

Val Glu Gln Ser Ile Arg Glu Lys Lys Ile Ser Ala Ile Phe Pro Asn
            260                 265                 270

Cys Val Ala Gly Thr Glu Ile Arg Ala Thr Leu Glu Ser Glu Gly Ala
        275                 280                 285

Arg Thr Leu Thr Trp Glu Thr Gln Arg Met Leu Asp Tyr Ser Leu Cys
    290                 295                 300

Gln Asn Thr Trp Asp Lys Val Ser Arg Lys Glu Pro Leu Ser Pro Leu
305                 310                 315                 320

Asp Leu Ser Tyr Leu Ser Pro Arg Ala Pro Gly Lys Gly Met Ala Tyr
                325                 330                 335

Thr Val Ile Asn Gly Thr Leu His Ser Ala His Ala Lys Tyr Ile Arg
            340                 345                 350

Thr Trp Ile Asp Tyr Gly Glu Met Lys Glu Ile Lys Gly Gly Arg Gly
        355                 360                 365

Glu Tyr Ser Lys Ala Pro Glu Leu Leu Trp Ser Gln Trp Phe Asp Phe
    370                 375                 380

Gly Pro Phe Lys Ile Gly Pro Asn Gly Leu Leu His Thr Gly Lys Thr
385                 390                 395                 400

Phe Lys Phe Pro Leu Tyr Leu Ile Gly Ala Gly Ile Ile Asp Glu Asp
                405                 410                 415

Leu His Glu Leu Asp Glu Ala Ala Pro Ile Asp His Pro Gln Met Pro
            420                 425                 430

Asp Ala Lys Ser Val Leu Pro Glu Asp Glu Glu Ile Phe Phe Gly Asp
        435                 440                 445

Thr Gly Val Ser Lys Asn Pro Ile Glu Leu Ile Gln Gly Trp Phe Ser
    450                 455                 460

Asn Trp Arg Glu Ser Val Met Ala Ile Val Gly Ile Val Leu Leu Ile
```

|  |  | 465 |  |  |  | 470 |  |  |  | 475 |  |  |  | 480 |  |
|---|---|---|---|---|---|---|---|---|---|---|---|---|---|---|---|

```
Val Val Thr Phe Leu Ala Ile Lys Thr Val Arg Val Leu Asn Cys Leu
                485                 490                 495

Trp Arg Pro Arg Lys Arg Ile Val Arg Gln Glu Val Asp Val Glu
            500                 505                 510

Ser Arg Leu Asn His Phe Glu Met Arg Gly Phe Pro Glu Tyr Val Lys
        515                 520                 525

Arg
```

(2) INFORMATION FOR SEQ ID NO: 9:

(i) SEQUENCE CHARACTERISTICS:
        (A) LENGTH: 1569 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 1..1566

(xi) SEQUENCE DESCRIPTION: SEQ ID NO: 9:

```
ATG AAT ATA CCT TGC TTT GCT GTG ATC CTC AGC TTA GCT ACT ACA CAT       48
Met Asn Ile Pro Cys Phe Ala Val Ile Leu Ser Leu Ala Thr Thr His
 1               5                  10                  15

TCT CTG GGA GAA TTC CCC TTG TAT ACG ATT CCC GAG AAA ATA GAG AAA       96
Ser Leu Gly Glu Phe Pro Leu Tyr Thr Ile Pro Glu Lys Ile Glu Lys
                20                  25                  30

TGG ACC CCC ATA GAC ATG ATC CAT CTT AGT TGC CCT AAT AAC ATG CTG      144
Trp Thr Pro Ile Asp Met Ile His Leu Ser Cys Pro Asn Asn Met Leu
            35                  40                  45

TCT GAG GAA GAA GGT TGC AAT ACA GAG TCT CCT TTC ACC TAC TTC GAG      192
Ser Glu Glu Glu Gly Cys Asn Thr Glu Ser Pro Phe Thr Tyr Phe Glu
        50                  55                  60

CTC AAG AGT GGT TAC CTA GCC CAT CAG AAG GTC CCA GGA TTT ACA TGC      240
Leu Lys Ser Gly Tyr Leu Ala His Gln Lys Val Pro Gly Phe Thr Cys
 65                  70                  75                  80

ACT GGG GTT GTG AAT GAG GCA GAG ACA TAC ACA AAC TTT GTC GGA TAT      288
Thr Gly Val Val Asn Glu Ala Glu Thr Tyr Thr Asn Phe Val Gly Tyr
                85                  90                  95

GTC ACC ACC ACC TTC AAA AGG AAG CAC TTT AAA CCT ACA GTG GCT GCT      336
Val Thr Thr Thr Phe Lys Arg Lys His Phe Lys Pro Thr Val Ala Ala
                100                 105                 110

TGT CGT GAT GCC TAC AAC TGG AAA GTA TCA GGG GAC CCC CGA TAT GAA      384
Cys Arg Asp Ala Tyr Asn Trp Lys Val Ser Gly Asp Pro Arg Tyr Glu
            115                 120                 125

GAA TCT CTA CAC ACC CCG TAT CCC GAC AGC AGC TGG TTA AGG ACT GTG      432
Glu Ser Leu His Thr Pro Tyr Pro Asp Ser Ser Trp Leu Arg Thr Val
        130                 135                 140

ACC ACA ACC AAA GAA GCC CTT CTT ATA ATA TCG CCA AGC ATT GTA GAG      480
Thr Thr Thr Lys Glu Ala Leu Leu Ile Ile Ser Pro Ser Ile Val Glu
145                 150                 155                 160

ATG GAC ATA TAT GGC AGG ACC CTT CAC TCT CCC ATG TTC CCT TCG GGG      528
Met Asp Ile Tyr Gly Arg Thr Leu His Ser Pro Met Phe Pro Ser Gly
                165                 170                 175

AAA TGT TCC AAG CTC TAT CCT TCT GTC CCC TCT TGT ACA ACC AAC CAT      576
Lys Cys Ser Lys Leu Tyr Pro Ser Val Pro Ser Cys Thr Thr Asn His
                180                 185                 190
```

```
GAT TAC ACA TTG TGG TTG CCA GAA GAT TCT AGT CTG AGT TTG ATT TGC      624
Asp Tyr Thr Leu Trp Leu Pro Glu Asp Ser Ser Leu Ser Leu Ile Cys
        195                 200                 205

GAC ATC TTC ACT TCC AGC AGT GGA CAG AAG GCC ATG AAT GGG TCT CGC      672
Asp Ile Phe Thr Ser Ser Ser Gly Gln Lys Ala Met Asn Gly Ser Arg
    210                 215                 220

ATC TGC GGA TTC AAG GAT GAA AGG GGA TTT TAC AGA TCC TTG AAG GGA      720
Ile Cys Gly Phe Lys Asp Glu Arg Gly Phe Tyr Arg Ser Leu Lys Gly
225                 230                 235                 240

TCC TGT AAG CTG ACA TTG TGC GGG AAA CCT GGA ATT AGG CTG TTC GAC      768
Ser Cys Lys Leu Thr Leu Cys Gly Lys Pro Gly Ile Arg Leu Phe Asp
            245                 250                 255

GGA ACT TGG GTC TCT TTT ACA AAG CCG GAC GTT CAT GTG TGG TGC ACT      816
Gly Thr Trp Val Ser Phe Thr Lys Pro Asp Val His Val Trp Cys Thr
                260                 265                 270

CCC AAC CAG TTA GTC AAT ATA CAT AAC GAC AGA CTA GAT GAG GTT GAA      864
Pro Asn Gln Leu Val Asn Ile His Asn Asp Arg Leu Asp Glu Val Glu
        275                 280                 285

CAT CTG ATC GTG GAC GAT ATC ATC AAG AAG AGA GAG GAG TGT TTA GAC      912
His Leu Ile Val Asp Asp Ile Ile Lys Lys Arg Glu Glu Cys Leu Asp
    290                 295                 300

ACG CTG GAA ACT ATA CTT ATG TCT CAA TCA GTT AGT TTT AGA CGG TTG      960
Thr Leu Glu Thr Ile Leu Met Ser Gln Ser Val Ser Phe Arg Arg Leu
305                 310                 315                 320

AGC CAT TTC AGA AAG TTA GTT CCA GGA TAT GGA AAA GCT TAC ACT ATT     1008
Ser His Phe Arg Lys Leu Val Pro Gly Tyr Gly Lys Ala Tyr Thr Ile
            325                 330                 335

TTG AAC GGC AGC TTA ATG GAA ACA AAT GTC TAC TAC AAA AGA GTT GAC     1056
Leu Asn Gly Ser Leu Met Glu Thr Asn Val Tyr Tyr Lys Arg Val Asp
                340                 345                 350

AGG TGG GCG GAC ATT TTG CCT TCT AGG GGA TGT CTG AAA GTC GGA CAA     1104
Arg Trp Ala Asp Ile Leu Pro Ser Arg Gly Cys Leu Lys Val Gly Gln
        355                 360                 365

CAG TGC ATG GAC CCT GTC AAA GGG GTC CTC TTC AAC GGA ATT ATC AAG     1152
Gln Cys Met Asp Pro Val Lys Gly Val Leu Phe Asn Gly Ile Ile Lys
    370                 375                 380

GGT CCG GAT GGA CAA ATA TTG ATT CCA GAG ATG CAG TCA GAG CAG CTC     1200
Gly Pro Asp Gly Gln Ile Leu Ile Pro Glu Met Gln Ser Glu Gln Leu
385                 390                 395                 400

AAA CAG CAT ATG GAT CTG TTG AAA GCA GCT ATG TTT CCT CTC CGT CAT     1248
Lys Gln His Met Asp Leu Leu Lys Ala Ala Met Phe Pro Leu Arg His
            405                 410                 415

CCT TTA ATC AAC AGA GAG GCA GTC TTC AAG AAG GAT GGA AAT GCC GAT     1296
Pro Leu Ile Asn Arg Glu Ala Val Phe Lys Lys Asp Gly Asn Ala Asp
                420                 425                 430

GAT TTT GTT GAT CTC CAT ATG CCT GAT GTT CAA AAA TCT GTG TCG GAT     1344
Asp Phe Val Asp Leu His Met Pro Asp Val Gln Lys Ser Val Ser Asp
        435                 440                 445

GTC GAC CTG GGC CTG CCT CAT TGG GGG TTC TGG TTG TTA GTC GGG GCA     1392
Val Asp Leu Gly Leu Pro His Trp Gly Phe Trp Leu Leu Val Gly Ala
    450                 455                 460

ACA GTA GTA GCC TTT GTG GTC TTG GCG TGC TTG CTC CGT GTA TGT TGT     1440
Thr Val Val Ala Phe Val Val Leu Ala Cys Leu Leu Arg Val Cys Cys
465                 470                 475                 480

AGG AGA ATG AGA AGG AGA AGG TCA CTG CGT GCC ACT CAG GAT ATC CCC     1488
Arg Arg Met Arg Arg Arg Arg Ser Leu Arg Ala Thr Gln Asp Ile Pro
            485                 490                 495

CTC AGC GTT GCC CCT GCC CCT GTC CCT CGT GCC AAA GTG GTG TCA TCA     1536
Leu Ser Val Ala Pro Ala Pro Val Pro Arg Ala Lys Val Val Ser Ser
                500                 505                 510
```

```
TGG GAG TCT TCT AAA GGG CTC CCA GGT ACT TGA                                1569
Trp Glu Ser Ser Lys Gly Leu Pro Gly Thr
    515                 520
```

(2) INFORMATION FOR SEQ ID NO: 10:

(i) SEQUENCE CHARACTERISTICS:
        (A) LENGTH: 522 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Asn Ile Pro Cys Phe Ala Val Ile Leu Ser Leu Ala Thr Thr His
 1               5                  10                  15

Ser Leu Gly Glu Phe Pro Leu Tyr Thr Ile Pro Glu Lys Ile Glu Lys
                20                  25                  30

Trp Thr Pro Ile Asp Met Ile His Leu Ser Cys Pro Asn Asn Met Leu
                35                  40                  45

Ser Glu Glu Gly Cys Asn Thr Glu Ser Pro Phe Thr Tyr Phe Glu
 50                  55                  60

Leu Lys Ser Gly Tyr Leu Ala His Gln Lys Val Pro Gly Phe Thr Cys
 65                  70                  75                  80

Thr Gly Val Val Asn Glu Ala Glu Thr Tyr Thr Asn Phe Val Gly Tyr
                85                  90                  95

Val Thr Thr Thr Phe Lys Arg Lys His Phe Lys Pro Thr Val Ala Ala
                100                 105                 110

Cys Arg Asp Ala Tyr Asn Trp Lys Val Ser Gly Asp Pro Arg Tyr Glu
                115                 120                 125

Glu Ser Leu His Thr Pro Tyr Pro Asp Ser Ser Trp Leu Arg Thr Val
 130                 135                 140

Thr Thr Thr Lys Glu Ala Leu Leu Ile Ile Ser Pro Ser Ile Val Glu
145                 150                 155                 160

Met Asp Ile Tyr Gly Arg Thr Leu His Ser Pro Met Phe Pro Ser Gly
                165                 170                 175

Lys Cys Ser Lys Leu Tyr Pro Ser Val Pro Ser Cys Thr Thr Asn His
                180                 185                 190

Asp Tyr Thr Leu Trp Leu Pro Glu Asp Ser Ser Leu Ser Leu Ile Cys
                195                 200                 205

Asp Ile Phe Thr Ser Ser Gly Gln Lys Ala Met Asn Gly Ser Arg
 210                 215                 220

Ile Cys Gly Phe Lys Asp Glu Arg Gly Phe Tyr Arg Ser Leu Lys Gly
225                 230                 235                 240

Ser Cys Lys Leu Thr Leu Cys Gly Lys Pro Gly Ile Arg Leu Phe Asp
                245                 250                 255

Gly Thr Trp Val Ser Phe Thr Lys Pro Asp Val His Val Trp Cys Thr
                260                 265                 270

Pro Asn Gln Leu Val Asn Ile His Asn Asp Arg Leu Asp Glu Val Glu
                275                 280                 285

His Leu Ile Val Asp Asp Ile Ile Lys Lys Arg Glu Glu Cys Leu Asp
 290                 295                 300

Thr Leu Glu Thr Ile Leu Met Ser Gln Ser Val Ser Phe Arg Arg Leu
305                 310                 315                 320

Ser His Phe Arg Lys Leu Val Pro Gly Tyr Gly Lys Ala Tyr Thr Ile
                325                 330                 335
```

-continued

```
Leu Asn Gly Ser Leu Met Glu Thr Asn Val Tyr Tyr Lys Arg Val Asp
            340                 345                 350

Arg Trp Ala Asp Ile Leu Pro Ser Arg Gly Cys Leu Lys Val Gly Gln
        355                 360                 365

Gln Cys Met Asp Pro Val Lys Gly Val Leu Phe Asn Gly Ile Ile Lys
    370                 375                 380

Gly Pro Asp Gly Gln Ile Leu Ile Pro Glu Met Gln Ser Glu Gln Leu
385                 390                 395                 400

Lys Gln His Met Asp Leu Leu Lys Ala Ala Met Phe Pro Leu Arg His
                405                 410                 415

Pro Leu Ile Asn Arg Glu Ala Val Phe Lys Lys Asp Gly Asn Ala Asp
                420                 425                 430

Asp Phe Val Asp Leu His Met Pro Asp Val Gln Lys Ser Val Ser Asp
        435                 440                 445

Val Asp Leu Gly Leu Pro His Trp Gly Phe Trp Leu Leu Val Gly Ala
    450                 455                 460

Thr Val Val Ala Phe Val Val Leu Ala Cys Leu Leu Arg Val Cys Cys
465                 470                 475                 480

Arg Arg Met Arg Arg Arg Arg Ser Leu Arg Ala Thr Gln Asp Ile Pro
                485                 490                 495

Leu Ser Val Ala Pro Ala Pro Val Pro Arg Ala Lys Val Val Ser Ser
                500                 505                 510

Trp Glu Ser Ser Lys Gly Leu Pro Gly Thr
            515                 520
```

METHODS FOR CREATING TRANSGENIC ANIMALS

CROSS-REFERENCE TO RELATED APPLICATIONS

This is a continuation of application Ser. No. 08/821,984 filed Mar. 20, 1997, now U.S. Pat. No. 6,080,912.

FIELD OF THE INVENTION

The present invention relates to improved methods for the generation of transgenic non-human animals. In particular, the present invention relates to the introduction of retroviral particles into the perivitelline space of gametes, zygotes and early stage embryos to allow the insertion of genetic material into the genome of the recipient gamete or embryo.

BACKGROUND

The ability to alter the genetic make-up of animals, such as domesticated mammals such as cows, pigs and sheep, allows a number of commercial applications. These applications include the production of animals which express large quantities of exogenous proteins in an easily harvested form (e.g., expression into the milk), the production of animals which are resistant to infection by specific microorganisms and the production of animals having enhanced growth rates or reproductive performance. Animals which contain exogenous DNA sequences in their genome are referred to as transgenic animals.

The most widely used method for the production of transgenic animals is the microinjection of DNA into the pronuclei of fertilized embryos. This method is efficient for the production of transgenic mice but is much less efficient for the production of transgenic animals using large mammals such as cows and sheep. For example, it has been reported that 1,000 to 2,000 bovine embryos at the pronuclear stage must be microinjected to produce a single transgenic cow at an estimate cost of more than $500,000 [Wall et al. (1992) J. Cell. Biochem. 49:113]. Furthermore, microinjection of pronuclei is more difficult when embryos from domestic livestock (e.g., cattle, sheep, pigs) is employed as the pronuclei are often obscured by yolk material. While techniques for the visualization of the pronuclei are known (i.e., centrifugation of the embryo to sediment the yolk), the injection of pronuclei is an invasive technique which requires a high degree of operator skill.

Alternative methods for the production include the infection of embryos with retroviruses or with retroviral vectors. Infection of both pre- and post-implantation mouse embryos with either wild-type or recombinant retroviruses has been reported [Janenich (1976) Proc. Natl. Acad. Sci. USA 73:1260–1264; Janenich et al. (1981) Cell 24:519; Stuhlmann et al. (1984) Proc. Natl. Acad. Sci. USA 81:7151; Jahner et al. (1985) Proc. Natl. Acad Sci. USA 82:6927–6931; Van der Putten, et al. (1985) Proc. Natl. Acad Sci. USA 82:6148–6152; Stewart, et al. (1987) EMBO J. 6:383–388]. The resulting transgenic animals are typically mosaic for the transgene since incorporation occurs only in a subset of cells which form the transgenic animal. The consequences of mosaic incorporation of retroviral sequences (i.e., the transgene) include lack of transmission of the transgene to progeny due to failure of the retrovirus to integrate into the germ line, difficulty in detecting the presence of viral sequences in the founder mice in those cases where the infected cell contributes to only a small part of the fetus and difficulty in assessing the effect of the genes carried on the retrovirus.

In addition to the production of mosaic founder animals, infection of embryos with retrovirus (which is typically performed using embryos at the 8 cell stage or later) often results in the production of founder animals containing multiple copies of the retroviral provirus at different positions in the genome which generally will segregate in the offspring. Infection of early mouse embryos by co-culturing early embryos with cells producing retroviruses requires enzymatic treatment to remove the zona pellucida [Hogan et al. (1994) in *Manipulating the Mouse Embryo: A Laboratory Manual*, 2nd Ed., Cold Spring Harbor Laboratory Press, Cold Spring Harbor, N.Y., pp. 251–252]. In contrast to mouse embryos, bovine embryos dissociate when removed from the zona pellucida. Therefore, infection protocols which remove the zona pellucida cannot be employed for the production of transgenic cattle or other animals whose embryos dissociate or suffer a significant decrease in viability upon removal of the zona pellucida (e.g., ovine embryos).

An alternative means for infecting embryos with retroviruses is the injection of virus or virus-producing cells into the blastocoele of mouse embryos [Jahner, D. et al. (1982) *Nature* 298:623–628]. As is the case for infection of eight cell stage embryos, most of the founders produced by injection into the blastocoele will be mosaic. The introduction of transgenes into the germline of mice has been reported using intrauterine retroviral infection of the midgestation mouse embryo [Jahner, D. et al. (1982) supra]. This technique suffers from a low efficiency of generation of transgenic animals and in addition produces animals which are mosaic for the transgene.

Infection of bovine and ovine embryos with retroviruses or retroviral vectors to create transgenic animals has been reported. These protocols involve the micro-injection of retroviral particles or growth arrested (i.e., mitomycin C-treated) cells which shed retroviral particles into the perivitelline space of fertilized eggs or early embryos [PCT International Application WO 90/08832 (1990) and Haskell and Bowen (1995) Mol. Reprod. Dev. 40:386]. PCT International Application WO 90/08832 describes the injection of wild-type feline leukemia virus B into the perivitelline space of sheep embryos at the 2 to 8 cell stage. Fetuses derived from injected embryos were shown to contain multiple sites of integration. The efficiency of producing transgenic sheep was low (efficiency is defined as the number of transgenics produced compared to the number of embryos manipulated); only 4.2% of the injected embryos were found to be transgenic.

Haskell and Bowen (supra) describe the micro-injection of mitomycin C-treated cells producing retrovirus into the perivitelline space of 1 to 4 cell bovine embryos. The use of virus-producing cells precludes the delivery of a controlled amount of viral particles per embryo. The resulting fetuses contained between 2 and 12 proviruses and were shown to be mosaic for proviral integration sites, the presence of provirus, or both. The efficiency of producing transgenic bovine embryos was low; only 7% of the injected embryos were found to be transgenic.

The art needs improved methods for the production of transgenic animals, particularly for the production of transgenics using large domestic livestock animals. The ideal method would be simple to perform and less invasive than pronuclear injection, efficient, would produce mosaic transgenic founder animals at a low frequency and would result in the integration of a defined number of copies of the introduced sequences into the genome of the transgenic animal.

SUMMARY OF THE INVENTION

The present invention provides improved methods and compositions for the production of transgenic non-human animals. In one embodiment, the present invention provides a composition comprising a non-human unfertilized oocyte comprising a heterologous oligonucleotide (i.e., a heterologous polynucleotide) integrated into the genome of the oocyte. In a preferred embodiment the unfertilized oocyte is a pre-maturation oocyte. In another preferred embodiment the unfertilized oocyte is a pre-fertilization oocyte. The present invention is not limited by the nature of the heterologous oligonucleotide contained within the genome of the oocyte. In a preferred embodiment, the heterologous oligonucleotide is the proviral form of a retroviral vector.

The invention is not limited by the nature of the retroviral vector employed. Retroviral vectors containing a variety of genes may be employed. For example, the retroviral vector may contain sequences encoding proteins which modify growth rate, size and/or carcass composition (e.g., bovine growth hormone or other growth hormones) or foreign proteins of commercial value that are expressed in, and harvested from, a particular tissue component (e.g., blood or milk). The retroviral vector may contain genes that confer disease resistance to viruses or other microorganisms, including DNA sequences that are transcribed into RNA sequences that catalytically cleave specific RNAs (ie., ribozymes) such as viral RNAs and DNA sequences that are transcribed into anti-sense RNA of an essential gene of a pathogenic microorganism. The above protein-encoding genes and DNA sequences are examples of "genes of interest."

The compositions of the present invention are not limited by the nature of the non-human animal employed to provide oocytes. In a preferred embodiment, the non-human animal is a mammal (e.g., cows, pigs, sheep, goats, rabbits, rats, mice, etc.). In a particularly preferred embodiment, the non-human animal is a cow.

The present invention further provides a method for introducing a heterologous polynucleotide into the genome of a non-human unfertilized oocyte, comprising: a) providing: i) a non-human unfertilized egg comprising an oocyte having a plasma membrane and a zona pellucida, the plasma membrane and the zona pellucida defining a perivitelline space; ii) an aqueous solution comprising a heterologous polynucleotide; and b) introducing the solution comprising the heterologous polynucleotide into the perivitelline space under conditions which permit the introduction of the heterologous polynucleotide into the genome of the oocyte. The method of the present invention is not limited by the nature of the heterologous polynucleotide employed. In a preferred embosiment, the heterologous polynucleotide encodes a protein of interest. In a particularly preferred embodiment, the heterologous polynucleotide is contained within genome of a recombinant retrovirus.

The method of the present invention may be practiced using unfertilized eggs comprising a pre-maturation oocyte. Alteratively, the method of the present invention may employ pre-fertilization oocytes as the unfertilized egg.

When a recombinant retrovirus is employed infectious retroviral particles comprising the heterologous polynucleotide are preferentially employed. The method of the present invention is not limited by the nature of the infectious retrovirus employed to deliver nucleic acid sequences to an oocyte. Any retrovirus which is capable of infecting the species of oocyte to be injected may be employed. In a preferred embodiment, the infectious retrovirus comprises a heterologous membrane-associated protein. In a preferred embodiment, the heterologous membrane-associated protein is a G glycoprotein selected from a virus within the family Rhabdoviridae. In another preferred embodiment, the heterologous membrane-associated protein is selected from the group consisting of the G glycoprotein of vesicular stomatitis virus, Piry virus, Chandipura virus, Spring viremia of carp virus and Mokola virus. In a particularly preferred embodiment, the heterologous membrane-associated protein is the G glycoprotein of vesicular stomatitis virus.

The method of the present invention is not limited by the nature of the non-human animal employed to provide oocytes. In a preferred embodiment, the non-human animal is a mammal (e.g., cows, pigs, sheep, goats, rabbits, rats, mice, etc.). In a particularly preferred embodiment, the non-human animal is a cow.

The present invention further provides a method for the production of a transgenic non-human animal comprising: a) providing: i) an unfertilized egg comprising an oocyte having a plasma membrane and a zona pellucida, the plasma membrane and the zona pellucida defining a perivitelline space; ii) an aqueous solution containing infectious retrovirus; b) introducing the solution containing infectious retrovirus into the perivitelline space under conditions which permit the infection of the oocyte; and c) contacting the infected oocyte with sperm under conditions which permit the fertilization of the infected oocyte to produce an embryo. In a preferred embodiment, the method of the present invention further comprises, following the fertilization of the infected oocyte, the step of transferring the embryo into a hormonally sychronized non-human recipient animal (i.e., a female animal hormonally sychronized to stimulate early pregnancy). In another preferred embodiment, the method comprises the step of allowing the transferred embryo to develop to term. In still another referred embodiment, at least one transgenic offspring is identified from the offspring allowed to develop to term.

The method of the present invention may be practiced using unfertilized eggs comprising a pre-maturation oocyte. Alteratively, the method of the present invention may employ pre-fertilization oocytes as the unfertilized egg.

When pre-maturation oocytes are employed in the method of the present invention, the method may further comprise, following the introduction of the solution containing infectious retrovirus into the pre-maturation oocyte, the further step of culturing the infected pre-maturation oocyte under conditions which permit the maturation of the pre-maturation oocyte. The art is well aware of culture conditions which permit the in vitro maturation of pre-maturation oocytes from a variety of mammalian species.

The method of the present invention is not limited by the nature of the infectious retrovirus employed to deliver nucleic acid sequences to an oocyte. Any retrovirus which is capable of infecting the species of oocyte to be injected may be employed. In a preferred embodiment, the infectious retrovirus comprises a heterologous membrane-associated protein. In a preferred embodiment, the heterologous membrane-associated protein is a G glycoprotein selected from a virus within the family Rhabdoviridae. In another preferred embodiment, the heterologous membrane-associated protein is selected from the group consisting of the G glycoprotein of vesicular stomatitis virus, Piry virus, Chandipura virus, Spring viremia of carp virus and Mokola virus. In a particularly preferred embodiment, the heterologous membrane-associated protein is the G glycoprotein of vesicular stomatitis virus.

The method of the present invention is not limited by the nature of the non-human animal employed to provide oocytes. In a preferred embodiment, the non-human animal is a mammal (e.g., cows, pigs, sheep, goats, rabbits, rats, mice, etc.). In a particularly preferred embodiment, the non-human animal is a cow.

DEFINITIONS

Figure 1:
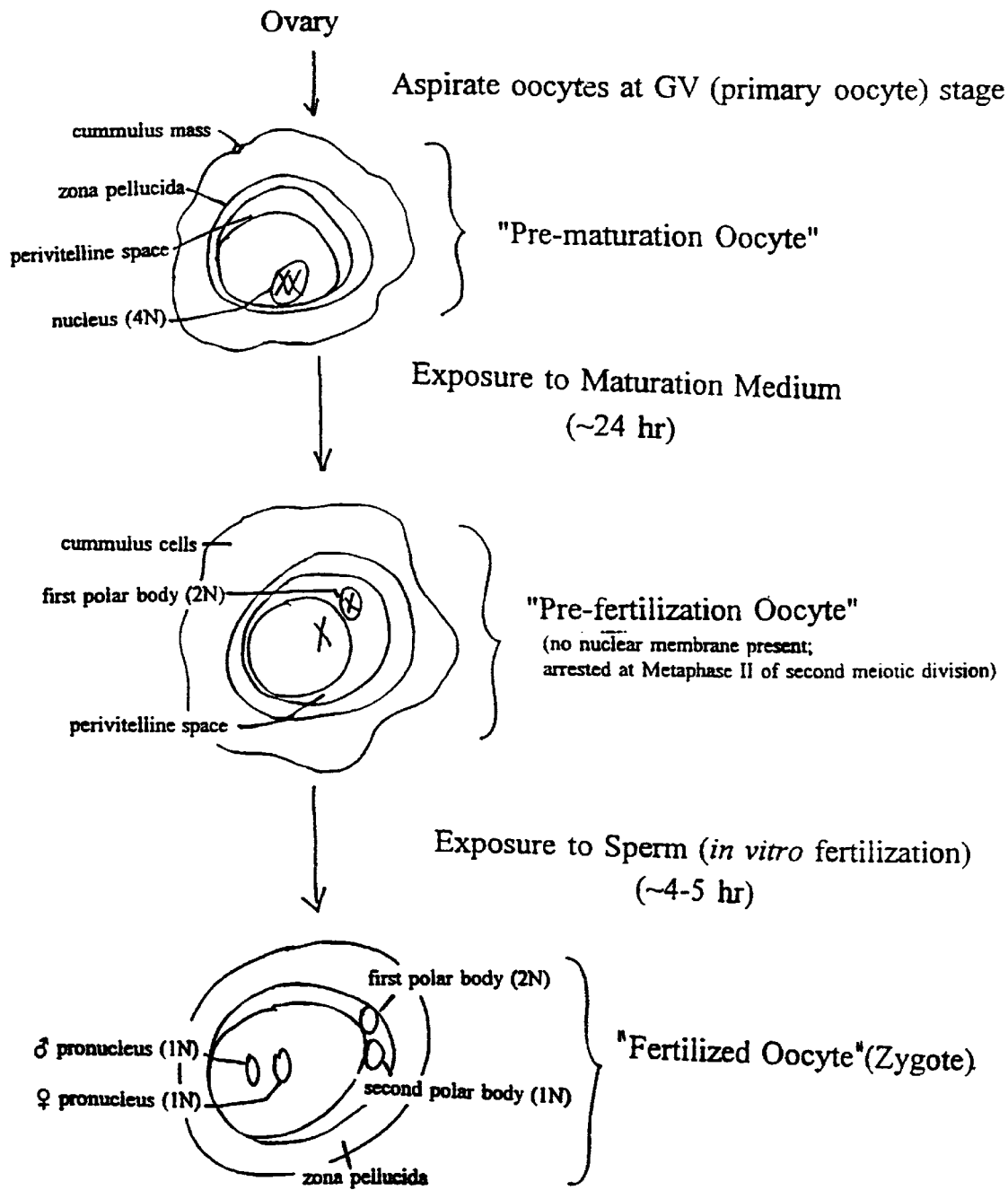
FIG. 1 provides a schematic showing the production of pre-maturation oocytes, pre-fertilization oocytes and fertilized oocytes (zygotes).

To facilitate understanding of the invention, a number of terms are defined below.

As used herein, the term "egg" when used in reference to a mammalian egg, means an oocyte surrounded by a zona-pellucida and a mass of cumulus cells (follicle cells) with their associated proteoglycan. The term "egg" is used in reference to eggs recovered from antral follicles in an ovary (these eggs comprise pre-maturation oocytes) as well as to eggs which have been released from an antral follicle (a ruptured follicle).

As used herein, the term "oocyte" refers to a female gamete cell and includes primary oocytes, secondary oocytes and mature, unfertilized ovum. An oocyte is a large cell having a large nucleus (i.e., the germinal vesicle) surrounded by ooplasm. The ooplasm contains non-nuclear cytoplasmic contents including mRNA, ribosomes, mitochondria, yolk proteins, etc. The membrane of the oocyte is referred to herein as the "plasma membrane."

The term "pre-maturation oocyte" as used herein refers to a female gamete cell following the oogonia stage (i.e., mitotic proliferation has occurred) that is isolated from an ovary (e.g., by aspiration) but which has not been exposed to maturation medium in vitro. Those of skill in the art know that the process of aspiration causes oocytes to begin the maturation process but that completion of the maturation process (i.e., formation of a secondary oocyte which has extruded the first polar body) in vitro requires the exposure of the aspirated oocytes to maturation medium. Pre-maturation oocytes will generally be arrested at the first anaphase of meiosis.

The term "pre-fertilization oocyte" as used herein refers to a female gamete cell such as a pre-maturation oocyte following exposure to maturation medium in vitro but prior to exposure to sperm (i.e., matured but not fertilized). The pre-fertilization oocyte has completed the first meiotic division, has released the first polar body and lacks a nuclear membrane (the nuclear membrane will not reform until fertilization occurs; after fertilization, the second meiotic division occurs along with the extrusion of the second polar body and the formation of the male and female pronuclei). Pre-fertilization oocytes may also be referred to as matured oocytes at metaphase II of the second meiosis.

The terms "unfertilized egg" or "unfertilized oocyte" as used herein refers to any female gamete cell which has not been fertilized and these terms encompass both pre-maturation and pre-fertilization oocytes.

The term "perivitelline space" refers to the space located between the zona pellucida and the plasma membrane of a mammalian egg or oocyte.

The term "infectious retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell.

Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells which are susceptible to infection by the retrovirus. Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell.

The terms "vector particle" or "retroviral particle" refer to viral-like particles that are capable of introducing nucleic acid into a cell through a viral-like entry mechanism.

The host range of a retroviral vector (i.e., the range of cells that these vectors can infect) can be altered by including an envelope protein from another closely related virus.

The term "membrane-associated protein" refers to a protein (e.g., a viral envelope glycoprotein or the G proteins of viruses in the Rhabdoviridae family such as VSV, Piry, Chandipura and Mokola) which are associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

The term "heterologous membrane-associated protein" refers to a membrane-associated protein which is derived from a virus which is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus Vesiculovirus which includes vesicular stomatitis virus (VSV), Cocal virus, Piry virus, Chandipura virus, and Spring viremia of carp virus (seqeunces encoding the Spring viremia of carp virus are available under GenBank accession number U18101). The G proteins of viruses in the Vesiculovirus genera are virally-encoded integral membrane proteins that form externally projecting homotrimeric spike glycoproteins complexes that are required for receptor binding and membrane fusion. The G proteins of viruses in the Vesiculovirus genera have a covalently bound palmititic acid ($C_{16}$) moiety. The amino acid sequences of the G proteins from the Vesiculoviruses are fairly well conserved. For example, the Piry virus G protein share about 38% identity and about 55% similarity with the VSV G proteins (several strains of VSV are known, e.g., Indiana, New Jersey, Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the Vesiculoviruses, the G proteins from non-VSV Vesiculoviruses may be used in place of the VSV G protein for the pseudotyping of viral particles. The G proteins of the Lyssa viruses (another genera within the Rhabdoviridae family) also share a fair degree of conservation with the VSV G proteins and function in a similar manner (e.g., mediate fusion of membranes) and therefore may be used in place of the VSV G protein for the pseudotyping of viral particles. The Lyssa viruses include the Mokola virus and the Rabies viruses (several strains of Rabies virus are known and their G proteins have been cloned and sequenced). The Mokola virus G protein shares stretches of homology (particulary over the extracellular and transmembrane domains) with the VSV G proteins which show about 31% identity and 48% similarity with the VSV G proteins. Preferred G proteins share at least 25% identity, preferably at least 30% identity and most preferably at least 35% identity with the VSV G proteins. The VSV G protein from which New Jesery strain (the sequence of this G protein is provided in GenBank accession numbers M27165 and M21557) is employed as the reference VSV G protein.

The term "conditions which permit the maturation of a pre-maturation oocyte" refers to conditions of in vitro cell culture which permit the maturation of a pre-maturation oocyte to a mature ovum (e.g., a pre-fertilization oocyte). These culture conditions permit and induce the events which are associated with maturation of the pre-maturation oocyte including stimulation of the first and second meiotic divisions. In vitro culture conditions which permit the maturation of pre-maturation oocytes from a variety of mammalian species (e.g., cattle, hamster, pigs and goats) are well know to the art [see e.g., Parrish et al. (1985) Theriogenology 24:537; Rosenkrans and First (1994) J. Ani. Sci. 72:434; Bavister and Yanagimachi (1977) Biol. Reprod. 16:228; Bavister et al. (1983) Biol. Reprod. 28:235; Leibfried and Bavister (1982) J. Reprod. Fert. 66:87; Keskintepe et al. (1994) Zygote 2:97 Funahashi et al. (1994) J. Reprod. Fert. 101:159 and Funahashi et al. (1994) Biol. Reprod 50:1072].

DESCRIPTION OF THE INVENTION

The present invention provides improved methods for the production of transgenic animals. The methods of the present invention provide, for the first time, the production of transgenic animals by the introduction of exogenous DNA into pre-maturation oocytes and mature, unfertilized oocytes (ie., pre-fertilization oocytes) using retroviral vectors which transduce dividing cells [e.g., vectors derived from murine leukemia virus (MLV)].

The Description of the Invention is divided into the following sections: I. Retroviruses and Retroviral Vectors; II. Integration of Retroviral DNA; III. Introduction of Retroviral Vectors Into Gametes Before the Last Meiotic Division; and IV. Detection of the Retrovirus Following Injection Into Oocytes or Embryos.

I. Retroviruses and Retroviral Vectors

Retroviruses (family Retroviridae) are divided into three groups: the spumaviruses (e.g., human foamy virus); the lentiviruses (e.g., human is immunodeficiency virus and sheep visna virus) and the oncoviruses (e.g., MLV, Rous sarcoma virus).

Retroviruses are enveloped (Le., surrounded by a host cell-derived lipid bilayer membrane) single-stranded RNA viruses which infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products) which is surrounded by a lipid bilayer membrane derived from the host cell containing the viral envelope glycoproteins (also referred to as membrane-associated proteins).

The organization of the genomes of numerous retroviruses is well known to the art and this has allowed the adaptation of the retroviral genome to produce retroviral vectors. The production of a recombinant retroviral vector carrying a gene of interest is typically achieved in two stages. First, the gene of interest is inserted into a retroviral vector which contains the sequences necessary for the efficient expression of the gene of interest [including promoter and/or enhancer elements which may be provided by the viral long terminal repeats (LTRs) or by an internal promoter/enhancer and relevant splicing signals], sequences required for the efficient packaging of the viral RNA into infectious virions [e.g., the packaging signal (Psi), the tRNA primer binding site (−PBS), the 3' regulatory sequences required for reverse transcription (+PBS)] and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes which are essential for viral replication (these essential genes are either deleted or disabled); the resulting virus is said to be replication defective.

Second, following the construction of the recombinant vector, the vector DNA is introduced into a packaging cell line. Packaging cell lines provide viral proteins required in trans for the packaging of the viral genomic RNA into viral particles having the desired host range (Le., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles which lack a membrane-associated protein (e.g., an env protein). In order to produce viral particles containing a membrane associated protein which will permit entry of the virus into a cell, the packaging cell line containing the retroviral sequences is transfected with sequences encoding a membrane-associated protein [e.g., the G protein of vesicular stomatitis virus (VSV)]. The transfected packaging cell will then produce viral particles which contain the membrane-associated protein expressed by the transfected packaging cell line; these viral particles which contain viral genomic RNA derived from one virus encapsidated by the envelope proteins of another virus are said to be pseudotyped virus particles.

Viral vectors, including recombinant retroviral vectors, provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

The most commonly used recombinant retroviral vectors are derived from the amphotropic Moloney murine leukemia virus (MoMLV) [Miller and Baltimore (1986) Mol. Cell. Biol. 6:2895]. The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly [Markowitz et al. (1988) J. Virol. 62:1120].

Despite these advantages, existing retroviral vectors based upon MoMLV are limited by several intrinsic problems: 1) they do not infect non-dividing cells [Miller et al., (1990) Mol. Cell. Biol. 10:4239], 2) they produce low titers of the recombinant virus [Miller and Rosman (1989) BioTechniques 7: 980 and Miller (1992) Nature 357: 455] and 3) they infect certain cell types (e.g., human lymphocytes) with low efficiency [Adams et al. (1992) Proc. Natl. Acad. Sci. USA 89:8981]. The low titers associated with MoMLV-based vectors has been attributed, at least in part, to the instability of the virus-encoded envelope protein. Concentration of retrovirus stocks by physical means (e.g., ultracentrifugation and ultrafiltration) leads to a severe loss of infectious virus.

The low titer and inefficient infection of certain cell types by MoMLV-based vectors has been overcome by the use of pseudotyped retroviral vectors which contain the G protein of VSV as the membrane associated protein. Unlike retroviral envelope proteins which bind to a specific cell surface protein receptor to gain entry into a cell, the VSV G protein interacts with a phospholipid component of the plasma membrane [Mastromarino et al. (1977) J. Gen. Virol. 68:2359]. Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity [Burns et al. (1993) Proc. Natl. Acad. Sci. USA 90:8033].

The VSV G protein has also been used to pseudotype retroviral vectors based upon the human immunodeficiency virus (HIV) [Naldini et al. (1996) Science 272:263]. Thus, the VSV G protein may be used to generate a variety of pseudotyped retroviral vectors and is not limited to vectors based on MoMLV.

The present invention is not limited to the use of the VSV G protein when a viral G protein is employed as the heterologous membrane-associated protein within a viral particle. The G proteins of viruses in the Vesiculovirus genera other than VSV, such as the Piry and Chandipura viruses, that are highly homologous to the VSV G protein and, like the VSV G protein, contain covalently linked palmitic acid [Brun et al. (1995) Intervirol. 38:274 and Masters et al. (1990) Virol. 171:285]; thus, the G protein of the Piry and Chandipura viruses can be used in place of the VSV G protein for the pseudotyping of viral particles. In addition, the VSV G proteins of viruses within the Lyssa virus genera such as Rabies and Mokola viruses show a high degree of conservation (amino acid sequence as well as functional conservation) with the VSV G proteins. For example, the Mokola virus G protein has been shown to function in a manner similar to the VSV G protein (i.e., to mediate membrane fusion) and therefore may be used in place of the VSV G protein for the pseudotyping of viral particles [Mebatsion et al. (1995) J. Virol. 69:1444]. The nucleotide sequence encoding the Piry G protein is provided in SEQ ID NO:5 and the amino acid sequence of the Piry G protein is provided in SEQ ID NO:6. The nucleotide sequence encoding the Chandipura G protein is provided in SEQ ID NO:7 and the amino acid sequence of the Chandipura G protein is provided in SEQ ID NO:8. The nucleotide sequence encoding the Mokola G protein is provided in SEQ ID NO:9 and the amino acid sequence of the Mokola G protein is provided in SEQ ID NO:10. Viral particles may be pseudotyped using either the Piry, Chandipura or Mokola G protein as described in Example 2 with the exception that a plasmid containing sequences encoding either the Piry, Chandipura or Mokola G protein under the transcriptional control of a suitable promoter element [e.g., the CMV intermediate-early promoter; numerous expression vectors containing the CMV IE promoter are available, such as the pcDNA3.1 vectors (Invitrogen)] is used in place of pHCMV-G. Sequences encoding other G proteins derived from other members of the Rhabdoviridae family may be used; sequences encoding numerous rhabdoviral G proteins are available from the GenBank database.

II. Integration of Retroviral DNA

The majority of retroviruses can transfer or integrate a double-stranded linear form of the virus (the provirus) into the genome of the recipient cell only if the recipient cell is cycling (i.e., dividing) at the time of infection. Retroviruses which have been shown to infect dividing cells exclusively, or more efficiently, include MLV, spleen necrosis virus, Rous sarcoma virus and human immunodeficiency virus (HIV; while HIV infects dividing cells more efficiently, HIV can infect non-dividing cells).

It has been shown that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus [Roe et al. (1993) EMBO J. 12:2099]. However, as integration does not occur in cells arrested in metaphase, the breakdown of the nuclear envelope alone may not be sufficient to permit viral integration; there may be additional requirements such as the state of condensation of the genomic DNA (Roe et al., supra).

III. Introduction of Retroviral Vectors into Gametes Before the Last Meiotic Division The nuclear envelope of a cell breaks down during meiosis as well as during mitosis. Meiosis occurs only during the final stages of gametogenesis. The methods of the present invention exploit the breakdown of the nuclear envelope during meiosis to permit the integration of recombinant retroviral DNA and permit for the first time the use of unfertilized oocytes (i.e., pre-fertilization and pre-maturation oocytes) as the recipient cell for retroviral gene transfer for the production of transgenic animals. Because infection of unfertilized oocytes permits the integration of the recombinant provirus prior to the division of the one cell embryo, all cells in the embryo will contain the proviral sequences.

Oocytes which have not undergone the final stages of gametogenesis are infected with the retroviral vector. The injected oocytes are then permitted to complete maturation with the accompanying meiotic divisions. The breakdown of the nuclear envelope during meiosis permits the integration of the proviral form of the retrovirus vector into the genome of the oocyte. When pre-maturation oocytes are used, the injected oocytes are then cultured in vitro under conditions which permit maturation of the oocyte prior to fertilization in vitro. Conditions for the maturation of oocytes from a number of mammalian species (e.g., bovine, ovine, porcine, murine, caprine) are well known to the art. In general, the base medium used herein for the in vitro maturation of bovine oocytes, TC-M199 medium, may be used for the in vitro maturation of other mammalian oocytes. TC-M199 medium is supplemented with hormones (e.g., luteinizing hormone and estradiol) from the appropriate mammalian species. The amount of time a pre-maturation oocyte must be exposed to maturation medium to permit maturation varies between mammalian species as is known to the art. For example, an exposure of about 24 hours is sufficient to permit maturation of bovine oocytes while porcine oocytes require about 44–48 hours.

Occytes may be matured in vivo and employed in place of oocytes matured in vitro in the practice of the present invention. For example, when porcine oocytes are to be employed in the methods of the present invention, matured pre-fertilization oocytes may be harvested directly from pigs that are induced to superovulate as is known to the art. Briefly, on day 15 or 16 of estrus the female pig(s) is injected with about 1000 units of pregnant mare's serum (PMS; available from Sigma and Calbiochem). Approximately 48 hours later, the pig(s) is injected with about 1000 units of human chorionic gonadotropin) (hCG; Sigma) and 24–48 hours later matured oocytes are collected from oviduct. These in vivo matured pre-fertlization oocytes are then injected with the desired retroviral preparation as described herein. Methods for the superovulation and collection of in vivo matured (ie., oocytes at the metaphase 2 stage) oocytes are known for a variety of mammals [e.g., for superovulation of mice, see Hogan et al. (1994), supra at pp. 130–133; for superovulation of pigs and in vitro fertilzation of pig oocytes see Cheng, W. (1995) Doctoral Dissertation, Cambridge University, Cambridge, United Kingdom].

Retroviral vectors capable of infecting the desired species of non-human animal which can be grown and concentrated to very high titers (e.g., $\geq 1 \times 10^8$ cfu/ml) are preferentially employed. The use of high titer virus stocks allows the introduction of a defined number of viral particles into the perivitelline space of each injected oocyte. The perivitelline space of most mammalian oocytes can accommodate about 10 picoliters of injected fluid (those in the art know that the volume that can be injected into the perivitelline space of a mammalian oocyte or zygote varies somewhat between species as the volume of an oocyte is smaller than that of a zygote and thus, oocytes can accommodate somewhat less than can zygotes).

The vector used may contain one or more genes encoding a protein of interest; alternatively, the vector may contain sequences which produce anti-sense RNA sequences or ribozymes. The infectious virus is microinjected into the perivitelline space of oocytes (including pre-maturation oocytes) or one cell stage zygotes. Microinjection into the perivitelline space is much less invasive than the microinjection of nucleic acid into the pronucleus of an embryo. Pronuclear injection requires the mechanical puncture of the plasma membrane of the embryo and results in lower embryo viability. In addition, a higher level of operator skill is required to perform pronuclear injection as compared to perivitelline injection. Visualization of the pronucleus is not required when the virus is injected into the perivitelline space (in contrast to injection into the pronucleus); therefore injection into the perivitelline space obviates the difficulties associated with visualization of pronuclei in species such as cattle, sheep and pigs.

The virus stock may be titered and diluted prior to microinjection into the perivitelline space so that the number of proviruses integrated in the resulting transgenic animal is controlled. The use of a viral stock (or dilution thereof) having a titer of $1 \times 10^8$ cfu/ml allows the delivery of a single viral particle per oocyte. The use of pre-maturation oocytes or mature fertilized oocytes as the recipient of the virus minimizes the production of animals which are mosaic for the provirus as the virus integrates into the genome of the oocyte prior to the occurrence of cell cleavage.

In order to deliver, on average, a single infectious particle per oocyte, the micropipets used for the injection are calibrated as follows. Small volumes (e.g., about 5–10 pl) of the undiluted high titer viral stock (e.g., a titer of about $1 \times 10^8$ cfu/ml) are delivered to the wells of a microtiter plate by pulsing the micromanipulator. The titer of virus delivered per a given number of pulses is determined by diluting the viral stock in each well and determining the titer using a suitable cell line (e.g., the 208F cell line) as described in Ex. 2. The number of pulses which deliver, on average, a volume of virus stock containing one infectious viral particle (i.e., gives a MOI of 1 when titered on 208F cells) are used for injection of the viral stock into the oocytes.

Prior to microinjection of the titered and diluted (if required) virus stock, the cumulus cell layer is opened to provide access to the perivitelline space. The cumulus cell layer need not be completely removed from the oocyte and indeed for certain species of animals (e.g., cows, sheep, pigs, mice) a portion of the cumulus cell layer must remain in contact with the oocyte to permit proper development and fertilization post-injection. Injection of viral particles into the perivitelline space allows the vector RNA (i.e., the viral genome) to enter the cell through the plasma membrane thereby allowing proper reverse transcription of the viral RNA.

IV. Detection of the Retrovirus Following Injection into Oocytes or Embryos

The presence of the retroviral genome in cells (e.g., oocytes or embryos) infected with pseudotyped retrovirus may be detected using a variety of means. The expression of the gene product(s) encoded by the retrovirus may be detected by detection of mRNA corresponding to the vector-encoded gene products using techniques well known to the art (e.g., Northern blot, dot blot, in situ hybridization and RT-PCR analysis). Direct detection of the vector-encoded gene product(s) is employed when the gene product is a protein which either has an enzymatic activity (e.g., β-galactosidase) or when an antibody capable of reacting with the vector-encoded protein is available.

Alternatively, the presence of the integrated viral genome may be detected using Southern blot or PCR analysis. For example, the presence of the LZRNL or LSRNL genomes may be detected following infection of oocytes or embryos using PCR as follows. Genomic DNA is extracted from the infected oocytes or embryos (the DNA may be extracted from the whole embryo or alternatively various tissues of the embryo may be examined) using techniques well known to the art. The LZRNL and LSRNL viruses contain the neo gene and the following primer pair can be used to amplify a 349-bp segment of the neo gene: upstream primer: 5'-GCATTGCATCAGCCATGATG-3' (SEQ ID NO:1) and downstream primer: 5'-GATGGATTGCACGCAGGTTC-3' (SEQ ID NO:2). The PCR is carried out using well known techniques [e.g., using a GeneAmp kit according to the manufacturer's instructions (Perkin-Elmer)]. The DNA present in the reaction is denatured by incubation at 94° C. for 3 min followed by 40 cycles of 94° C. for 1 min, 60° C. for 40 sec and 72° C. for 40 sec followed by a final extension at 72° C. for 5 min. The PCR products may be analyzed by electrophoresis of 10 to 20% of the total reaction on a 2% agarose gel; the 349-bp product may be visualized by staining of the gel with ethidium bromide and exposure of the stained gel to UV light. If the expected PCR product cannot be detected visually, the DNA can be transferred to a solid support (e.g., a nylon membrane) and hybridized with a $^{32}$P-labeled neo probe.

Southern blot analysis of genomic DNA extracted from infected oocytes and/or the resulting embryos, offspring and tissues derived therefrom is employed when information concerning the integration of the viral DNA into the host genome is desired. To examine the number of integration sites present in the host genome, the extracted genomic DNA is typically digested with a restriction enzyme which cuts at least once within the vector sequences. If the enzyme chosen cuts twice within the vector sequences, a band of known (i.e., predictable) size is generated in addition to two fragments of novel length which can be detected using appropriate probes.

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); μM(micromolar); nM (nanomolar); mol (moles); mmol (millimoles); μmol (micromoles); nmol (nanomoles); gm (grams); mg (milligrams); μg (micrograms);pg (picograms); L (liters); ml (milliliters); μl (microliters); cm (centimeters); mm (millimeters); μm (micrometers); nm (nanometers); 0° C. (degrees Centigrade); AMP (adenosine 5'-monophosphate); BSA (bovine serum albumin); cDNA (copy or complimentary DNA); CS (calf serum); DNA (deoxyribonucleic acid); ssDNA (single stranded DNA); dsDNA (double stranded DNA); dNTP (deoxyribonucleotide triphosphate); LH (luteinizing hormone); NIH (Natioal Institues of Health, Besthesda, MD); RNA (ribonucleic acid); PBS (phosphate buffered saline); g (gravity); OD (optical density); HEPES (N-[2-Hydroxyethyl]piperazine-N-[2-ethanesulfonic acid]); HBS (HEPES buffered saline); PBS (phosphate buffered saline); SDS (sodium dodecylsulfate); Tris-HCl (tris [Hydroxymethyl]aminomethane-hydrochloride); Klenow (DNA polymerase I large (Klenow) fragment); rpm (revolutions per minute); EGTA (ethylene glycol-bis(β-aminoethyl ether) N, N, N', N'-tetraacetic acid); EDTA (ethylenediaminetetracetic acid); bla (β-lactamase or ampicillin-resistance gene); ORI (plasmid origin of replication); lacI (lac repressor); X-gal (5-bromo-4-chloro-3-indolyl-β-D-galactoside); ATCC (American Type Culture Collection, Rockville, Md.); GIBCO/BRL (GIBCO/BRL, Grand Island, N.Y.); Perkin-Elmer (Perkin-Elmer, Norwalk, Conn.); and Sigam (Sigma Chemical Company, St. Louis, Mo.).

Example 1

Generation of Cell Lines Stably Expressing the MoMLV gag and pol Proteins

The expression of the fusogenic VSV G protein on the surface of cells results in syncytium formation and cell death. Therefore, in order to produce retroviral particles containing the VSV G protein as the membrane-associated protein a three step approach was taken. First, stable cell lines expressing the gag and pol proteins from MoMLV at high levels were generated (e.g., 293GP cells; Example 1). These stable cell lines were then infected using the desired retroviral vector which is derived from an amphotrophic packaging cell (e.g., PA317 cells transfected with the desired retroviral vector; Example 2a). The infected stable cell line which expresses the gag and pol proteins produces noninfectious viral particles lacking a membrane-associated protein (e.g., a envelope protein). Third, these infected cell lines are then transiently transfected with a plasmid capable of directing the high level expression of the VSV G protein (Example 2b). The transiently transfected cells produce VSV G-pseudotyped retroviral vectors which can be collected from the cells over a period of 3 to 4 days before the producing cells die as a result of syncytium formation.

The first step in the production of VSV G-pseudotyped retroviral vectors, the generation of stable cell lines expressing the MoMLV gag and pol proteins is described below.

The human adenovirus 5-transformed embryonal kidney cell line 293 (ATCC CRL 1573) was cotransfected with the pCMVgag-pol and pFR400 plasmids using a ratio of 10:1 (pCMVgag-pol and pFR400). pCMV gag-pol contains the MoMLV gag and pol genes under the control of the CMV promoter (pCMV gag-pol is available from the ATCC). pFR400 encodes a mutant dihydrofolate reductase which has a reduced affinity for methotrexate [Simonsen et al., Proc. Natl. Acad. Sci. 80:2495 (1983)].

The plasmid DNA was introduced into the 293 cells using calcium phosphate co-precipitation [Graham and Van der Eb, Virol. 52:456 (1973)]. Approximately $5 \times 10^5$ 293 cells were plated into a 100 mm tissue culture plate the day before the DNA co-precipitate was added. A total of 20 μg of plasmid DNA (18 μg pCMV gag-pol and 2 μg pFR400) was added as a calcium-DNA co-precipitate to each 100 mm plate. Stable transformants were selected by growth in DMEM-high glucose medium containing 10% FCS, 0.5 μM methotrexate and 5 μM dipyridimole (selective medium). Colonies which grew in the selective medium were screened for extracellular reverse transcriptase activity [Goff et al., J. Virol. 38:239 (1981)] and intracellular p30$^{gag}$ expression. p30$^{gag}$ expression was determined by Western blotting using a goat-anti p30 antibody (NCI antiserum 77S000087). A clone which exhibited stable expression of the retroviral genes in the absence of continued methotrexate selection was selected. This clone was named 293GP (293 gag-pol). The 293GP cell line, a derivative of the human Ad-5-transformed embryonal kidney cell line 293, was grown in DMEM-high glucose medium containing 10% FCS. The 293GP cell line is commercially available from Viagen, Inc., San Diego, Calif.

Example 2

Preparation of Pseudotyped Retroviral Vectors Bearing the G Glycoprotein of VSV

In order to produce VSV G protein pseudotyped retrovirus the following steps were taken. First, the 293GP cell line was infected with virus derived from the amphotrophic packaging cell line PA317. The infected cells packaged the retroviral RNA into viral particles which lack a membrane-associated protein (because the 293GP cell line lacks an env gene or other gene encoding a membrane-associated protein). The infected 293GP cells were then transiently transfected with a plasmid encoding the VSV G protein to produce pseudotyped viral particles bearing the VSV G protein.

a) Cell Lines and Plasmids

The amphotropic packaging cell line, PA317 (ATCC CRL 9078) was grown in DMEM-high glucose medium containing 10% FCS. The 293GP cell line was grown in DMEM-high glucose medium containing 10% FCS. The titer of the pseudo-typed virus may be determined using either 208F cells [Quade (1979) Virol. 98:461] or NIH/3T3 cells (ATCC CRL 1658); 208F and NIH/3T3 cells are grown in DMEM-high glucose medium containing 10% CS.

The plasmid pLZRNL [Xu et al. (1989) Virol. 171:331] contains the gene encoding E. coli β-galactosidase (LacZ) under the transcriptional control of the LTR of the Moloney murine sarcoma virus (MSV) followed by the gene encoding neomycin phosphotransferase (Neo) under the transcriptional control of the Rous sarcoma virus (RSV) promoter. The plasmid pLSRNL contains the gene encoding the hepatitis B surface antigen gene (HBsAg) under the transcriptional control of the MSV LTR followed by the Neo gene under the control of the RSV promoter (U.S. Pat. No. 5,512,421, the disclosure of which is herein incorporated by reference). The plasmid pHCMV-G contains the VSV G gene under the transcriptional control of the human cytomegalovirus intermediate-early promoter [Yee et al. (1994) Meth. Cell Biol. 43:99].

b) Production and Titering of Pseudotyped LZRNL Virus pLZRNL DNA was transfected into the amphotropic packaging line PA317 to produced LZRNL virus. The resulting LZRNL virus was then used to infect 293GP cells to produce pseudotyped LZRNL virus bearing the VSV G protein (following transient transfection of the infected 293GP cells with a plasmid encoding the VSV G protein). The procedure for producing pseudotyped LZRNL virus was carried out as described [Yee et al. (1994) Meth. Cell Biol. 43:99].

Briefly, on day 1, approximately $5\times10^5$ PA317 cells were placed in a 100 mm tissue culture plate. On the following day (day 2), the PA317 cells were transfected with 20 µg of pLZRNL plasmid DNA (plasmid DNA was purified using CsCl gradients) using the standard calcium phosphate co-precipitation procedure [Graham and Van der Eb (1973) Virol. 52:456]. A range of 10 to 40 µg of plasmid DNA may be used. Because 293GP cells may take more than 24 hours to attach firmly to tissue culture plates, the 293GP cells may be placed in 100 mm plates 48 hours prior to transfection. The transfected PA317 cells provide amphotropic LZRNL virus.

On day 3, approximately $1\times10^5$ 293GP cells were placed in a 100 mm tissue culture plate 24 hours prior to the harvest of the amphotropic virus from the transfected PA317 cells. On day 4, culture medium was harvested from the transfected PA317 cells 48 hours after the application of the pLZRNL DNA. The culture medium was filtered through a 0.45 µm filter and polybrene was added to a final concentration of 8 µg/ml. A stock solution of polybrene was prepared by dissolving 0.4 gm hexadimethrine bromide (polybrene; Sigma) in 100 ml sterile water; the stock solution was stored at 4° C. The culture medium containing LZRNL virus (containing polybrene) was used to infect the 293GP cells as follows. The culture medium was removed from the 293GP cells and was replaced with the LZNRL virus containing culture medium. The virus containing medium was allowed to remain on the 293GP cells for 16 hours. Following the 16 hour infection period (on day 5), the medium was removed from the 293GP cells and was replaced with fresh medium containing 400 µg/ml G418 (GIBCO/BRL). The medium was changed every 3 days until G418-resistant colonies appeared two weeks later. Care was taken not to disturb the G418-resistant colonies when the medium was changed as 293GP cells attach rather loosely to tissue culture plates.

The G418-resistant 293 colonies were picked using an automatic pipettor and transferred directly into 24-well plates (ie., the colonies were not removed from the plates using trypsin). The G418-resistant 293 colonies (as termed "293GP/LZRNL" cells) were screened for the expression of the LacZ gene in order to identify clones which produce high titers of pseudotyped LZRNL virus. Clones in 24-well plates were transferred to 100 mm tissue culture plates and allowed to grow to confluency. Protein extracts are prepared from the confluent plates by washing the cells once with 10 ml PBS (137 mM NaCl, 2.6 mM KCl, 8.1 mM $Na_2HPO_4$, 1.5 mM $KH_2PO_4$). Two ml of 250 mM Tris-HCl, pH 7.8 was added and the cells were scrapped off the plate using a rubber policeman. The cells were then collected by centrifugation at room temperature and resuspended in 100 µl 250 mM Tris-HCl, pH 7.8. The cells were subjected to four rapid freeze/thaw cycles followed by centrifugation at room temperature to remove cell debris. The β-galactosidase activity present in the resulting protein extracts was determined as follows. Five microliters of protein extract was mixed with 500 µl β-gal buffer (50 mM Tris-HCl, pH 7.5, 100 mM NaCl, 10 mM $MgCl_2$) containing 0.75 ONPG (Sigma). The mixtures were incubated at 37° C. until a yellow color appeared. The reactions were stopped by the addition of 500 µl 10 mM EDTA and the optical density of the reactions was determined at 420 nm.

The 293GP/LZRNL clone which generated the highest amount of β-galactosidase activity was then expanded and used subsequently for the production of pseudotyped LZNRL virus as follows. Approximately $1\times10^6$ 293GP/LZRNL cells were placed into a 100 mm tissue culture plate. Twenty-four hours later, the cells were transfected with 20 µg of pHCMV-G plasmid DNA using calcium phosphate co-precipitation. Six to eight hours after the calcium-DNA precipitate was applied to the cells, the DNA solution was replaced with fresh culture medium (lacking G418). Longer transfection times (overnight) have been found to result in the detachment of the majority of the 293GP/LZRNL cells from the plate and are therefore avoided. The transfected 293GP/LZRNL cells produce pseudotyped LZRNL virus.

The pseudotyped LZRNL virus generated from the transfected 293GP/LZRNL cells can be collected at least once a day between 24 and 96 hr after transfection. The highest virus titer was generated approximately 48 to 72 hr after initial pHCMV-G transfection. While syncytium formation became visible about 48 hr after transfection in the majority of the transfected cells, the cells continued to generate pseudotyped virus for at least an additional 48 hr as long as the cells remained attached to the tissue culture plate. The collected culture medium containing the VSV G-pseudotyped LZRNL virus was pooled, filtered through a 0.45 $\mu$m filter and stored at $-70°$ C.

The titer of the VSV G-pseudotyped LZRNL virus was then determined as follows. $5\times10^5$ rat 208F fibroblasts or NIH 3T3 cells were plated in a 100 mm culture plate. Twenty-fours hours after plating, the cells were infected with serial dilutions of the LZRNL virus-containing culture medium in the presence of 8 $\mu$g/ml polybrene. Sixteen hours after infection with virus, the medium was replaced with fresh medium containing 400 $\mu$g/ml G418 and selection was continued for 14 days until G418-resistant colonies became visible. Viral titers were typically about 0.5 to $5\times10^6$ colony forming units (cfu)/ml. The titer of the virus stock could be concentrated to a titer of greater than $10^9$ cfu/ml as described below.

Example 3

Concentration of Pseudotyped Retroviral Vectors

The VSV G-pseudotyped LZRNL virus was concentrated to a high titer by two cycles of ultracentrifugation. The frozen culture medium collected as described in Example 2 which contained pseudotyped LZRNL virus was thawed in a 37° C. water bath and was then transferred to ultraclear centrifuge tubes (14×89 mm; Beckman, Palo Alto, Calif.) which had been previously sterilized by exposing the tubes to UV light in a laminar flow hood overnight. The virus was sedimented in a SW41 rotor (Beckman) at 50,000×g (25,000 rpm) at 4° C. for 90 min. The culture medium was then removed from the tubes in a laminar flow hood and the tubes were well drained. The virus pellet was resuspended to 0.5 to 1% of the original volume of culture medium in either TNE (50 mM Tris-HCl, pH 7.8; 130 mM NaCl; 1 mM EDTA) or 0.1×Hank's balanced salt solution [1×Hank's balanced salt solution contains 1.3 mM $CaCl_2$, 5 mM KCl, 0.3 mM $KH_2PO_4$, 0.5 mM $MgCl_2.6H_2$), 0.4 mM $MgSO_4.7H_2O$, 138 mM NaCl, 4 mM $NaHCO_3$, 0.3 mM $NaH_2PO_4.H_2O$; 0.1×Hank's is made by mixing 1 parts 1×Hank's with 9 parts PBS]. The resuspended virus pellet was incubated overnight at 4° C. without swirling. The virus pellet could be dispersed with gentle pipetting after the overnight incubation without significant loss of infectious virus. The titer of the virus stock was routinely increase 100- to 300-fold after one round of ultracentrifugation. The efficiency of recovery of infectious virus varied between 30 and 100%.

The virus stock was then subjected to low speed centrifugation in a microfuge for 5 min at 4° C. to remove any visible cell debris or aggregated virions that were not resuspended under the above conditions (if the virus stock is not to be used for injection into oocytes or embryos, this centrifugation step may be omitted).

The virus stock was then subjected to another round of ultracentrifugation to concentrate the virus stock further. The resuspended virus from the first round of centrifugation was pooled and pelleted by a second round of ultracentrifugation which was performed as described above. Viral titers were increased approximately 2000-fold after the second round of ultracentrifugation (titers of the pseudotyped LZRNL virus were typically greater than or equal to $1\times10^9$ cfu/ml after the second round of ultracentrifugation).

The titers of the pre- and post-centrifugation fluids were determined by infection of 208F (NIH 3T3 or Mac-T cells can also be employed) followed by selection of G418-resistant colonies as described above in Example 2. The concentrated viral stock was stable (ie., did not lose infectivity) when stored at 4° C. for several weeks.

Example 4

Preparation of Pseudotyped Retrovirus For Infection of Oocytes and Embryos

The concentrated pseudotyped retrovirus were resuspended in 0.1×HBS (2.5 mM HEPES, pH 7.12, 14 mM NaCl, 75 $\mu$M $Na_2HPO_4.H_2O$) and 18 $\mu$l aliquots were placed in 0.5 ml vials (Eppendorf) and stored at $-80°$ C. until used. The titer of the concentrated vector was determined by diluting 1 $\mu$l of the concentrated virus $10^{-7}$- or $10^{-8}$-fold with 0.1×HBS. The diluted virus solution was then used to infect 208F and Mac-T cells and viral titers were determined as described in Example 2.

Prior to infection of oocytes or embryos (by microinjection), 1 $\mu$l of polybrene [25 ng/$\mu$l; the working solution of polybrene was generated by diluting a stock solution having a concentration of 1 mg/ml (in sterile $H_2O$) in 0.1 HBS, pH 7.12] was mixed with 4 $\mu$l of concentrated virus to yield a solution containing $10^3$–$10^4$ cfu/$\mu$l and 8 $\mu$g/ml polybrene. This solution was loaded into the injection needle (tip having an internal diameter of approximately 2–4 $\mu$m) for injection into the perivitelline space of gametes (pre-maturation oocytes, matured oocytes) or one cell stage zygotes (early stage embryo). An Eppendorf Transjector 5246 was used for all microinjections.

Example 5

Preparation and Microinjection of Gametes and Zygotes

Gametes (pre-maturation and pre-fertilization oocytes) and zygotes (fertilized oocytes) were prepared and microinjected with retroviral stocks as described below.

a) Solutions

Tyrodes-Lactate with HEPES (TL-HEPES): 114 mM NaCl, 3.2 mM KCl, 2.0 mM $NaHCO_3$, 0.4 mM $Na_2H_2PO_4.H_2O$, 10 mM Na-lactate, 2 mM $CaCl_2.2H_2O$, 0.5 mM $MgCl_2.6H_2O$, 10 mM HEPES, 100 IU/ml penicillin, 50 $\mu$g/ml phenol red, 1 mg/ml BSA fraction V, 0.2 mM pyruvate and 25 $\mu$g/ml gentamycin.

Maturation Medium: TC-199 medium (GIBCO) containing 10% FCS, 0.2 mM pyruvate, 5 $\mu$g/ml NIH o-LH (NIH), 25 $\mu$g/ml gentamycin and 1 $\mu$g/ml estradiol-17$\beta$.

Sperm-Tyrodes-Lactate (Sperm-TL): 100 mM NaCl, 3.2 mM KCl, 25 mM $NaHCO_3$, 0.29 mM $Na_2H_2PO_4.H_2O$, 21.6 mM Na-lactate, 2.1 mM $CaCl_2.2H_2O$, 0.4 mM $MgCl_2.6H_2O$, 10 mM HEPES, 50 $\mu$g/ml phenol red, 6 mg/ml BSA fraction V, 1.0 mM pyruvate and 25 $\mu$g/ml gentamycin.

Fertilization Medium: 114 mM NaCl, 3.2 mM KCl, 25 mM $NaHCO_3$, 0.4 mM $Na_2H_2PO_4.H_2O$, 10 mM Na-lactate, 2 mM $CaCl_2.2H_2O$, 0.5 mM $MgCl_2.6H_2O$, 100 IU/ml penicillin, 50 $\mu$g/ml phenol red, 6 mg/ml BSA fatty acid free, 0.2 mM pyruvate and 25 $\mu$g/ml gentamycin.

PHE: 1 mM hypotaurine, 2 mM penicillamine and 250 μM epinephrine.

Embryo Incubation+Amino Acids (EIAA): 114 μM NaCl, 3.2 μM KCl, 25 μM NaHCO$_3$, 1.6 μg/ml L(+)-lactate, 10.7 μg/ml L-glutamine, 300 μg/ml BSA fatty acid free, 0.275 μg/ml pyruvate, 25 μg/ml gentamycin, 10 μl of 100×MEM amino acids stock (M7145, Sigma) per ml and 20 μl of 50×BME amino acids stock (B6766, Sigma) per ml.

0.1×HBS: 2.5 mM HEPES (pH 7.12), 14 mM NaCl and 75 μM Na$_2$HPO$_4$.H$_2$O.

b) Preparation, Injection, Maturation and Fertilization of Pre-Maturation Oocytes Oocytes were aspirated from small antral follicles on ovaries from dairy cattle obtained from a slaughterhouse. Freshly aspirated oocytes at the germinal vesicle (GV) stage, meiosis arrested, with the cumulus mass attached were selected (i.e., pre-maturation oocytes). The oocytes were then washed twice in freshly prepared TL-HEPES and transferred into a 100 μl drop of TL-HEPES for microinjection.

Concentrated retroviral particles (prepared as described in Example 3) were resuspended in 0.1×HBS, mixed with polybrene and loaded into the injection needle as described in Example 4. Approximately 10 pl of the virus solution was then injected into the perivitelline space of pre-maturation oocytes.

Following injection, the pre-maturation oocytes were washed twice in fresh TL-HEPES and transferred into maturation medium (10 oocytes in 50 μl). The pre-maturation oocytes were then incubated in Maturation Medium for 24 hours at 37° C. which permits the oocytes to mature to the metaphase II stage. The matured oocytes were then washed twice in Sperm-TL and 10 oocytes were then transferred into 44 μl of Fertilization Medium. The mature oocytes (10 oocytes/44 μl Fertilization Medium) were then fertilized by the addition of 2 μl of sperm at a concentration of 2.5×10$^7$/ml, 2 μl of PHE and 2 μl of heparin (fertilization mixture). Sperm was prepared by discontinuous percoll gradient separation of frozen-thawed semen as described [Kim et al. (1993) Mol. Reprod. Develop. 35:105]. Briefly, percoll gradients were formed by placing 2 ml of each of 90% and 45% percoll in a 15 ml conical tube. Frozen-thawed semen was layered on top of the gradient and the tubes were centrifuged for 10 minutes at 700×g. Motile sperm were collected from the bottom of the tube.

The oocytes were incubated for 16 to 24 hours at 37° C. in the fertilization mixture. Following fertilization, the cumulus cells were removed by vortexing the cells (one cell stage zygotes, Pronucleus Stage) for 3 minutes to produce "nude" oocytes. The nude oocytes were then washed twice in embryo culture medium (EIAA) and 20 to 25 zygotes were then cultured in 50 μl drop of EIAA (without serum until Day 4 at which time the zygotes were placed in EIAA containing 10% serum) until the desired developmental stage was reached: approximately 48 hours or Day 2 (Day 0 is the day when the matured oocytes are co-cultured with sperm) for morula stage (8 cell stage) or Day 6–7 for blastocyst stage. Embryos at the morula stage were analyzed for expression of β-galactosidase as described in Example 6. Embryos derived from injected pre-maturation oocytes were also analyzed for β-galactosidase expression at the 2 cell, 4 cell, and blastocyst stage and all developmental stages examined were positive.

c) Preparation, Injection and Fertilization of Pre-Fertilization Oocytes

Pre-maturation oocytes were harvested, washed twice with TL-HEPES as described above. The oocytes were then cultured in Maturation Medium (10 oocytes per 50 μl medium) for 16 to 20 hours to produce pre-fertilization oocytes (Metaphase II Stage). The pre-fertilization or matured oocytes were then vortexed for 3 minutes to remove the cumulus cells to produce nude oocytes. The nude oocytes were washed twice in TL-HEPES and then transferred into a 100 μl drop of TL-HEPES for microinjection. Microinjection was conducted as described above.

Following microinjection, the pre-fertilization oocytes were washed twice with TL-HEPES and then placed in Maturation Medium until fertilization. Fertilization was conducted as described above. Following fertilization, the zygotes were then washed twice in EIAA and 20 to 25 zygotes were then cultured per 50 μl drop of EIAA until the desired developmental stage was reached. The embryos were then examined for β-galactosidase expression (Ex. 6) or transferred to recipient cows (Ex. 7).

d) Preparation and Injection of One-Cell Stage Zygotes

Matured oocytes (Metaphase II stage) were generated as described above. The matured oocytes were then co-cultured in the presence of sperm for 16 to 20 hours as described above to generate zygotes at the pronucleus stage. Zygotes at the pronucleus stage were vortexed for 3 minutes to remove the cumulus cell layer prior to microinjection. Microinjection of retrovirus was conducted as described above. Following microinjection, the zygotes were washed four times in EIAA and then placed in an EIAA culture drop (25 zygotes per 50 μl drop of EIAA). The zygotes were cultured in EIAA (20 to 25 zygote per 50 μl drop of EIAA) until the desired developmental stage was reached. The embryos were then examined for β-galactosidase expression (Ex. 6) or transferred to recipient cows (Ex. 7).

Example 6

Injection of Pseudotyped Retrovirus into the Perivitelline Space of Maturing Bovine Oocytes Results in the Efficient Transfer of Vector Sequences Oocytes and one-cell zygotes which had been microinjected with pseudotyped LZRNL virus and cultured in vitro were examined for expression of vector sequences by staining for β-galactosidase activity when the embryos had reached the morula stage. β-galactosidase activity was examined as follows. Embryos were washed twice in PBS then fixed in 0.5% glutaraldehyde in PBS containing 2mM MgCl$_2$ for 40 min. at 4° C. The fixed embryos were then washed three times with PBS containing 2 mM MgCl$_2$ and then incubated at 37° C. overnight in X-gal solution (20 mM K$_3$Fe(CN)$_6$, 20 mM K$_4$Fe(CN)6.H$_2$O, 2 mM MgCl$_2$ and 1 mg/ml X-gal). The presence of a blue precipitate indicates expression of β-galactosidase activity. The results are shown in Table 1 below.

TABLE 1

| Stage at Injection | Stage at Analysis | % Positive For β-galactosidase Expression |
|---|---|---|
| Pre-Fertilization Oocyte (injected 20–24 hrs after exposure to Maturation Medium) | Morula | 47 (80/172)[a] |
| Pronuclei Stage (injected 18–20 hrs after exposure to sperm) | Morula | 25 (20/80) |
| One-Cell Zygote | Morula | 25 (20/80) |

[a]Number positive/number injected.

From the results shown in Table 1, it is clear that infection of pre-fertilization oocytes and zygotes using the methods of the present invention results in the transfer and expression of retrovirally encoded nucleic acid. While not limiting the present invention to any particular theory, it is currently believed that only half of the daughter cells from an initial founder cell infected with a retrovirus will contain the provirus because the retroviral provirus integrates into post-replication host DNA [Hajihosseini et al. (1993) EMBO J. 12:4969]. Therefore, the finding that 47% of the injected pre-fertilization oocytes are positive for β-galactosidase expression suggests that 100% of these injected oocytes were infected with the recombinant retrovirus. Therefore, the methods of the present invention provide an efficiency of generating transgenic embryos which is superior to existing methods.

Example 7

Generation of Transgenic Cows Containing Integrated Retroviral Nucleic Acid Sequences Embryos derived from infected pre-fertilization oocytes and early zygotes were transferred into recipient cows which were allowed to progress to term as described below.

a) Treatment of Embryos Derived from Infected Oocytes and Zygotes

Pre-fertilization oocytes (infected about 17 hours after exposure to Maturation Medium) and early stage zygotes (≦8 cell stage) were prepared and infected as described in Example 5 with the exceptions that 1) the VSV-G-pseudotyped virus used was the LSRNL virus which was prepared as described for the LZRNL virus in Ex. 2 and 2) at day 4 post-fertilization, embryos derived from injected pre-fertilization oocytes and zygotes were placed in freshly prepared EIAA medium containing 10% FCS and allowed to develop in vitro until transfer into recipient cows. Embryos at Day 7 were transferred into recipient females which were prepared as described below.

b) Preparation of Recipient Cows and Embryo Transfer

Recipients cows were synchronized by injecting 100 µg of gonadotropin-releasing hormone (GnRH; Sanofi Winthrop Pharmaceutical Inc., New York, N.Y.) (Day 0). Seven days later, the recipients were injected with 25 mg of PGF2α (Upjohn Co., Kalamazoo, Mich.). Thirty to 48 hours after injection of PGF2α, a second injection of 100 µg of GnRH was given. Ovulation occurs about 24–32 hours post injection. Seven days after ovulation occurred, embryos derived from infected oocytes and zygotes (Day 7 embryos) were then transferred nonsurgically to the uteri the recipient cows. Two embryos were transferred into each recipient (it is expected that only one calf will be born from the transfer of two embryos into a single recipient).

A total of 20 embryos were transferred into recipients on three separate days. In the first transfer 8 embryos derived from infected pre-fertilization oocytes were transferred into 4 recipients; four calves were born to these recipients and all four were found to be positive for the presence of vector proviral DNA (i.e., 100% were transgenic). In the second transfer 8 embryos derived from pre-fertilization oocytes were transferred into 4 recipients; 2 calves were born to these recipients and one of these animals was found to be transgenic (in the second transfer, one pregnancy was lost in the first month and another pregnancy comprising twins was lost in the eighth month; neither embryo from the 8 month pregnancy was transgenic). In the third transfer 4 embryos derived from infected zygotes (infected at the 4–8 cell stage) were transferred into 2 recipients; 3 calves were born to these recipients and none were transgenic.

The nine calves appeared healthy at birth and continue to appear healthy at the age of 6 months. Following the birth of offspring derived from the injected oocytes and zygotes, the offspring were examined by Southern blot and PCR analyses to determine whether they contained the retroviral transgenes and whether they exhibited somatic cell mosaicism. Skin tissue and white blood cells (buffy coat) was collected from the calves. Genomic DNA was extracted using standard techniques. Briefly, the tissue samples were digested with 50 µg/ml proteinase K (GIBCO) at 55° C. The samples were then extracted sequentially twice with an equal volume of phenol, once with phenol:chloroform (1:1) and once with chloroform. The DNA present in the aqueous layer was then precipitated by the addition of 2 volumes of isopropanol. The DNA was collected by centrifugation and the DNA pellet was resuspended in TE buffer (10 mM Tris-Cl, 1 mM EDTA, pH 8.0) and the concentration was determined spectrophotometrically. The DNA was then analyzed by Southern blotting and PCR analysis. The results are shown in FIGS. 2 and 3.

Figure 2:
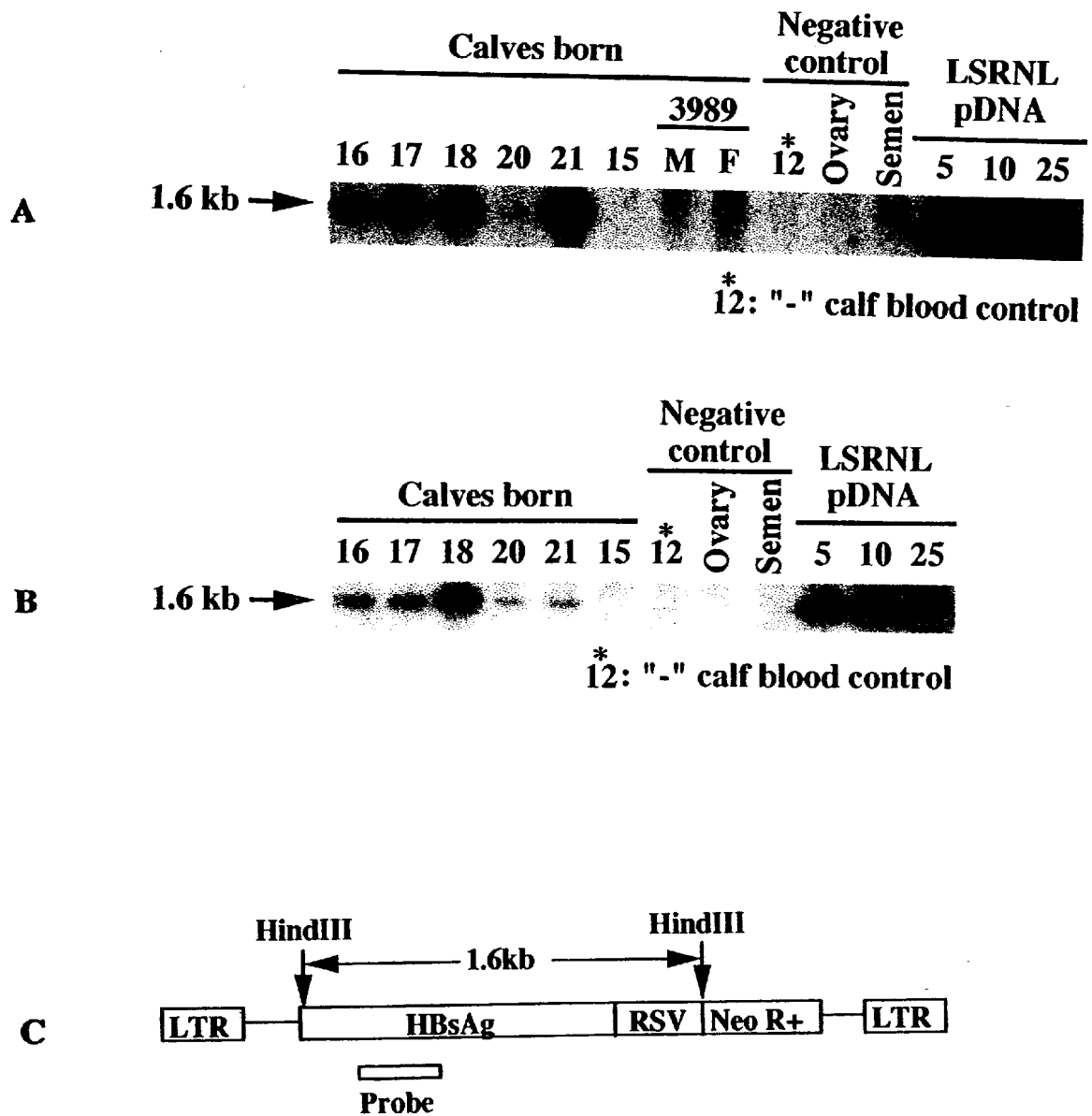
FIG. 2(A–C) shows an autoradiogram of a Southern blot of genomic DNA isolated from the skin (A) and blood (B) of calves derived from pre-fertilization oocytes and zygotes which were injected with pseudotyped LSRNL retrovirus (C).
Figure 3:
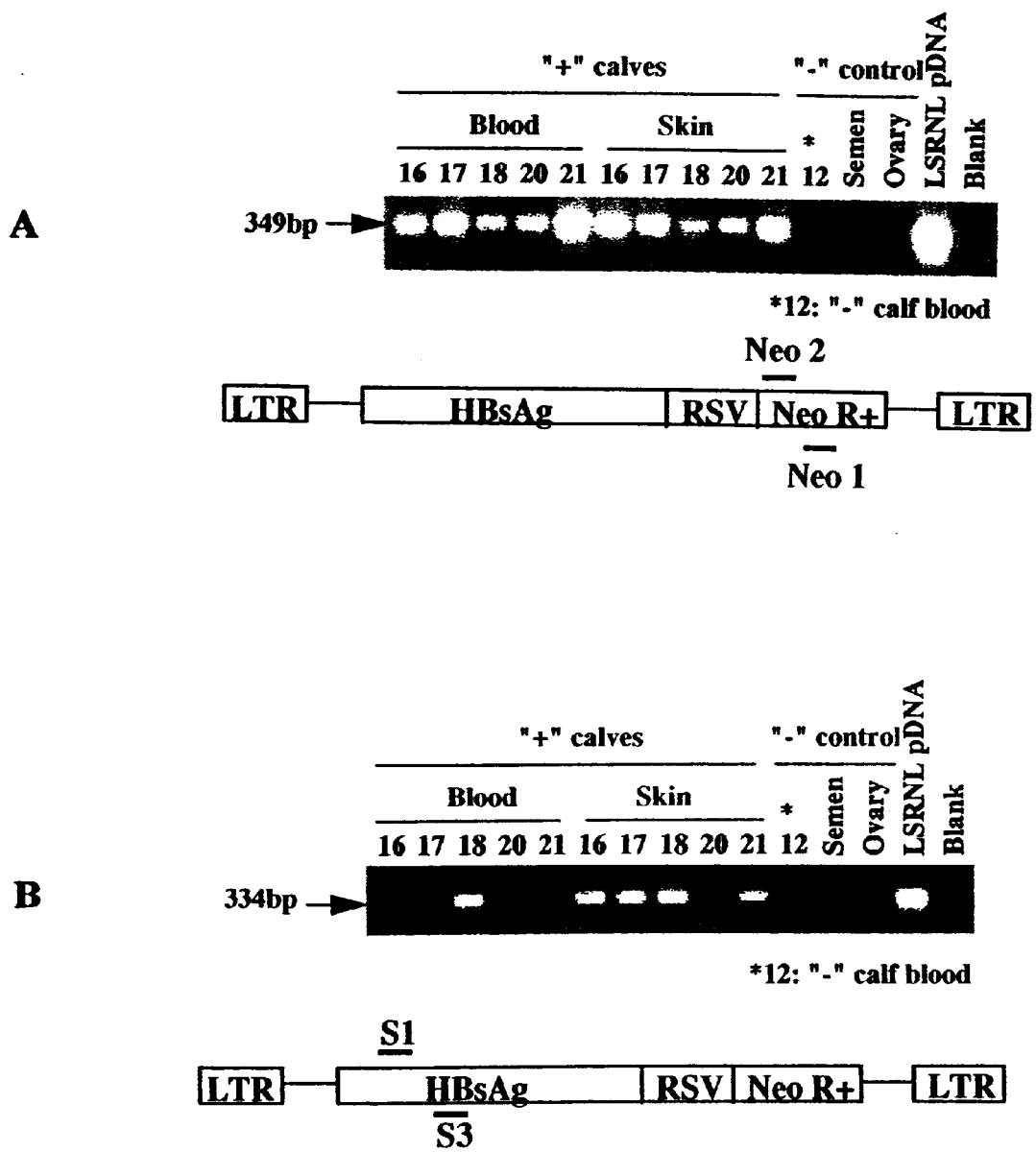
FIG. 3 (A–B) shows an ethidium bromide stained agarose gel containing electrophoresed PCR products which were amplified using neo gene primers (A) or HBsAg primers (B) from the blood and skin of calves derived from pre-fertilization oocytes and zygotes injected with pseudotyped LSRNL retrovirus.

FIG. 2 shows an autoradiography of a Southern blot of genomic DNA isolated from the skin (FIG. 2A) and blood (FIG. 2B) of the six calves derived from either pre-fertilization oocytes infected with VSV G-pseudotyped LSRNL virus at about 17 hours after exposure to Maturation Medium (calves numbered 17, 18, 20 and 21) or one cell zygotes infected at about 12 hrs post-fertilization (calves numbered 15 and 16). The calf DNA was digested with HindIII which cuts the pLSRNL vector twice to generate a 1.6 kb fragment (FIG. 2C). HindIII-digested DNA from the blood (lane labelled *12 derived from a randon, nontransgenic calf), ovary and semen of nontransgenic cows (derived random adult females and males) were also included. Lanes labeled "3989 M and F" represent DNA derived from two late term embryos that were born one month prematurely (these calves were generated from injected fertilized eggs and both are nontransgenic). Lanes labelled "LSRNL pDNA" contain HindIII-digested pLSRNL plasmid DNA and provide controls for the quantitiation of the copy number of the integrated proviruses in the offspring (DNA equivalent to 5, 10 or 25 copies of LSRNL were applied in these lanes).

Approximately 10 µg of the HindIII-digested DNAs were electrophoresed on 0.8% agarose gels, and blotted onto a nylon membrane. The membrane was hybridized with a $^{32}$P-labelled probe which hybridizes to the HBsAg gene present in the pLZRNL vector (FIG. 2C). The HBsAG probe was generated by PCR amplification of pLSRNL plasmid DNA using the upstream primer S-1 [5'-GGCTATCGCTGGATGTGTCT-3' (SEQ ID NO:3)] and the downstream primer S-3 [5'-ACTGAACAAATGGCACTAGT-3' (SEQ ID NO:4)]. The PCR-generated probe (334 bp) was labeled using a Rediprime kit (Amersham, Arlington Heights, Ill.) according to the manufacturer's instructions. The autoradiographs shown in FIG. 2 were generated by exposure of the blots to X-ray film for 3 weeks at −80° C.

The results shown in FIG. 2 demonstrates that calves 16, 17, 18, 20 and 21 contained retroviral vector DNA in both the skin (FIG. 2A) and blood (FIG. 2B). As blood cells (buffy coat) are derived from the mesoderm and skin cells are derived from the ectoderm, these results show that the transgenic animals do not display somatic cell mosaicism. Southern blotting analysis has shown that the majority (i.e., 7/9) of the transgenic calves contain a single copy of the proviral sequence; a few (i.e., 2/9) animals appear to contain two copies of the integrated proviral sequence. These results further demonstrate that retroviral infection of both pre-fertilization oocytes and early stage zygotes was successful in integrating the viral sequences into the genome of the resulting transgenic animals.

In order to confirm the presence of integrated retroviral sequences in the genome of the transgenic animals' somatic cells, PCR analysis (FIG. 3) was performed using genomic DNA isolated from the five transgenic calves which were determined by Southern blot analysis to be transgenic for the retroviral sequences. FIG. 3 shows the results of the PCR analysis following amplification of two different regions (i.e., the neo gene and the HBsAg gene) of the LZRNL retroviral genome which was injected into the oocytes. Genomic DNA from the skin and blood of each of the five transgenic calves was amplified using the upstream and downstream primers (SEQ ID NOS:1 and 2 and NOS:3 and 4; described supra) for the neo (FIG. 3A) and HBsAg (FIG. 3B) genes, respectively. The PCRs were conducted using the following thermocycling conditions: 94° C. ( 4 min); [94° C. (2 min); 50° C. (2 min); 72° C. min)]$_{30\ cycles}$; 72° C. (10 min). Amplification yielded the expected size of amplified sequence with the neo (349 bp) and HBsAg (334 bp) primers in both the blood and skin of each of the five transgenic calves. Genomic DNA isolated from the blood of non-transgenic calves as well as from semen and ovary of non-transgenic cattle were used as negative controls in the PCRS. pLSRNL DNA was used as the positive control.

These data demonstrate that the infection of pre-fertilization oocytes results in the efficient transfer of retroviral vector DNA (100% or 4 transgenic calves/4 calves born from embryos derived from infected pre-fertilization oocytes). In addition to providing a means for efficiently generating transgenic animals. The methods of the present invention provide a means for generating transgenic animals which do not display somatic cell mosaicism. Further, these methods permit the production of transgenic animals which contain a single copy of the transgene.

In order to confirm germ line transmission of the integrated viral sequences, the transgenic offspring are bred with non-transgenic cattle and the presence of the viral sequences (i.e., the transgene) is determined using Southern blot analysis or PCR amplification as described above. Animals which are heterozygous or homozygous for the transgene are produced using methods well known to the art (e.g., interbreeding of animals heterozygous for the transgene).

From the above it is clear that the invention provides improved methods and compositions for the production of transgenic non-human animals. The methods of the present invention provide for the production of transgenic non-human animals with improved efficiency and a reduced incidence of generating animals which are mosaic for the presence of the transgene.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A method for the production of a transgenic bovine embryo comprising:
   a) providing:
      i) a bovine unfertilized egg;
      ii) an aqueous solution containing infectious retrovirus which includes a polynucleotide encoding a protein of interest;
   b) introducing said solution containing infectious retrovirus into said oocyte under conditions which permit the infection of sad oocyte, thereby giving an infected oocyte; and
   c) contacting said infected oocyte with sperm under conditions which permit the fertilization of said infected oocyte to produce an embryo, said embryo comprising a copy of the polynucleotide integrated therein.

2. The method of claim 1 further comprising following the fertilization of said infected oocyte the step of transferring said embryo into a non-human female mammalian recipient that is hormonally synchronized to simulate early pregnancy, thereby giving a transferred embryo.

3. The method of claim 2 further comprising the step of allowing said embryo to develop to term.

4. The method of claim 3 further comprising identifying at least one transgenic offspring.

5. The method of claim 1, wherein said unfertilized egg comprises a pre-maturation oocyte.

6. The method of claim 1, wherein said unfertilized egg comprises an pre-fertilization oocyte.

7. The method of claim 5 further comprising following the introduction of said solution containing infectious retrovirus into said pre-maturation oocyte, the further step of culturing said infected pre-maturation oocyte under conditions which permit the maturation of said pre-maturation oocyte, thereby giving a matured oocyte.

8. The method of claim 1, wherein said infectious retrovirus comprises a heterologous membrane-associated protein.

9. The method of claim 8, wherein said heterologous membrane-associated protein is G glycoprotein selected from a virus within the family Rhabdoviridae.

10. The method of claim 9, wherein said G glycoprotein is selected from the group consisting of the G glycoprotein of vesicular stomatitis virus, Piry virus, Chandipura virus, Spring viremia of carp virus, Rabies virus and Mokola virus.

11. The method of claim 1, wherein said oocyte lacks a nuclear envelope.

* * * * *